US011142499B1

(12) United States Patent
Qi et al.

(10) Patent No.: US 11,142,499 B1
(45) Date of Patent: Oct. 12, 2021

(54) METHOD OF PREPARING 5R-[(BENZYLOXY) AMINO] PIPERIDINE-2S-CARBOXYLIC ACID OR A DERIVATIVE THEREOF

(71) Applicant: XINFA PHARMACEUTICAL CO., LTD, Dongying (CN)

(72) Inventors: Yuxin Qi, Dongying (CN); Xinfa Li, Dongying (CN); Xin Xu, Dongying (CN); Baolin Wang, Dongying (CN); Hu Qu, Dongying (CN); Shungen Xie, Dongying (CN)

(73) Assignee: XINFA PHARMACEUTICAL CO., LTD, Dongying (CN)

( * ) Notice: Subject to any disclaimer, the term of this patent is extended or adjusted under 35 U.S.C. 154(b) by 408 days.

(21) Appl. No.: 16/345,765

(22) PCT Filed: Mar. 6, 2018

(86) PCT No.: PCT/CN2018/078072
§ 371 (c)(1),
(2) Date: Apr. 29, 2019

(87) PCT Pub. No.: WO2019/127902
PCT Pub. Date: Jul. 4, 2019

(30) Foreign Application Priority Data

Dec. 28, 2017 (CN) .......................... 201711456332.0

(51) Int. Cl.
*C07D 211/60* (2006.01)
*C07D 211/02* (2006.01)

(52) U.S. Cl.
CPC .......... *C07D 211/60* (2013.01); *C07D 211/02* (2013.01)

(58) Field of Classification Search
CPC ........................... C07D 211/60; C07D 211/02
See application file for complete search history.

(56) References Cited

U.S. PATENT DOCUMENTS

2012/0053350 A1* 3/2012 Mangion .............. C07D 471/08
546/121

* cited by examiner

*Primary Examiner* — Timothy R Rozof
(74) *Attorney, Agent, or Firm* — CBM Patent Consulting, LLC

(57) ABSTRACT

The present application relates to methods of preparing 5R-[(benzyloxy) amino] piperidine-2S-carboxylic acid or its derivatives in an environment-friendly way. The method uses L-glutamic acid as a starting material, which is first subjected to esterification reaction in the presence of an acidic reagent, and then reacted successively with 2-haloacetate and N-protecting agent, or with N-protecting agent and 2-haloacetate under a basic condition to obtain compound IV; then, the obtained compound IV is subjected to intramolecular condensation into a ring under the action of a strong base to obtain N-protecting group piperidine-5-one-2S-carboxylate (V).

10 Claims, 2 Drawing Sheets

METHOD OF PREPARING 5R-[(BENZYLOXY) AMINO] PIPERIDINE-2S-CARBOXYLIC ACID OR A DERIVATIVE THEREOF

FIELD

The present application relates to the field of pharmaceutical and biochemical engineering, and more specifically relates to a green method of preparing 5R-[(benzyloxy) amino] piperidine-2S-carboxylic acid or a derivative thereof, wherein the compound is a key intermediate for preparing avibactam and relebactam.

BACKGROUND

Avibactam and relebactam are diazabicyclooctanone compounds, as non-β-lactam inhibitors, wherein avibactam may inhibit type-A (including ESBL and KPC) and type C β-lactamases; when co-administered with various types of cephalosporins and carbapenem antibiotics, avibactam has a broad-spectrum activity against bacteria, particularly has a significant activity against the *Escherichia coli* and *Klebsiella pneumoniae* containing extended-spectrum β-lactamases, *Escherichia coli* containing surplus AmpC enzyme, and *Escherichia coli* containing both AmpC and extended-spectrum β-lactamases. A combined medicine of relebactam and imipenem-cilastatin sodium exhibits a good performance in phase II clinical trial. The CAS number of avibactam ($I_a$) is 1192491-61-4, with a chemical name of [(1R,2S,5R)-2-(aminocarbonyl)-7-oxo-1,6-diazabicyclo [3.2.1]oct-6-yl] sodium sulphate; the CAS number of relebactam ($I_b$) is 1174018-99-5, with a chemical name of [(1R,2S,5R)-2-(N-(4-piperidyl)aminocarbonyl)-7-oxo-1,6-diazabicyclo[3.2.1]oct-6-yl] sulfuric acid. Structures of the avibactam, relebactam, and their key intermediates are provided below:

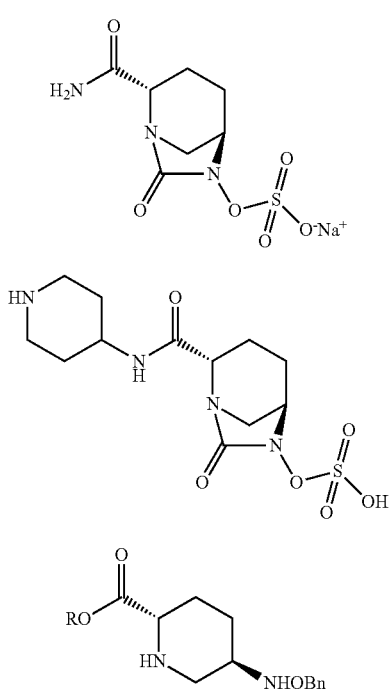

5R-[(benzyloxy) amino] piperidine-2S-carboxylate ($II_a$), 5R-[(benzyloxy) amino] piperidine-2S-carboxylate oxalate ($II_c$), and 5R-[(benzyloxy) amino] piperidine-2S-carboxylic acid ($II_b$) are key intermediates for preparing avibactam and relebactam. The patent WO2012172368 disclosed a method of synthesizing 5R-[(benzyloxy)amino] piperidine-2S-carboxylate ($II_a$), 5R-[(benzyloxy)amino] piperidine-2S-carboxylic acid, and avibactam; the U.S. Patents US2010197928 and US2013012712 specifically disclosed synthesis of 5R-[(benzyloxy) amino] piperidine-2S-carboxylate ($II_a$), as shown in Scheme 1. The technical solution of the Scheme 1 comprises: with N-protected L-pyroglutamic acid ester as the starting material, opening the ring thereof by trimethyl sulfoxide iodide to extend carbon chain, converting the carbonyl to imine by benzyloxyamine, removing the protecting group in an acidic condition, closing the ring in a basic condition, and finally reducing by a reductant, and chiral resolution, thereby obtaining the product 5R-[(benzyloxy) amino] piperidine-2S-carboxylate ($II_a$). The N-protected L-pyroglutamic acid ester, trimethyl sulfoxide iodide, and methanesulfonic acid used as starting materials in the methods are expensive; with dimethyl sulfoxide as the solvent, post-treatment produces a large amount of wastewater, such that the methods have a poor environment-friendliness and a relatively low total yield (59%).

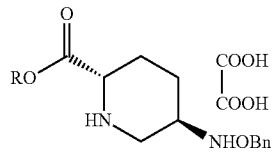

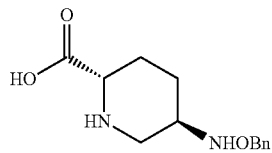

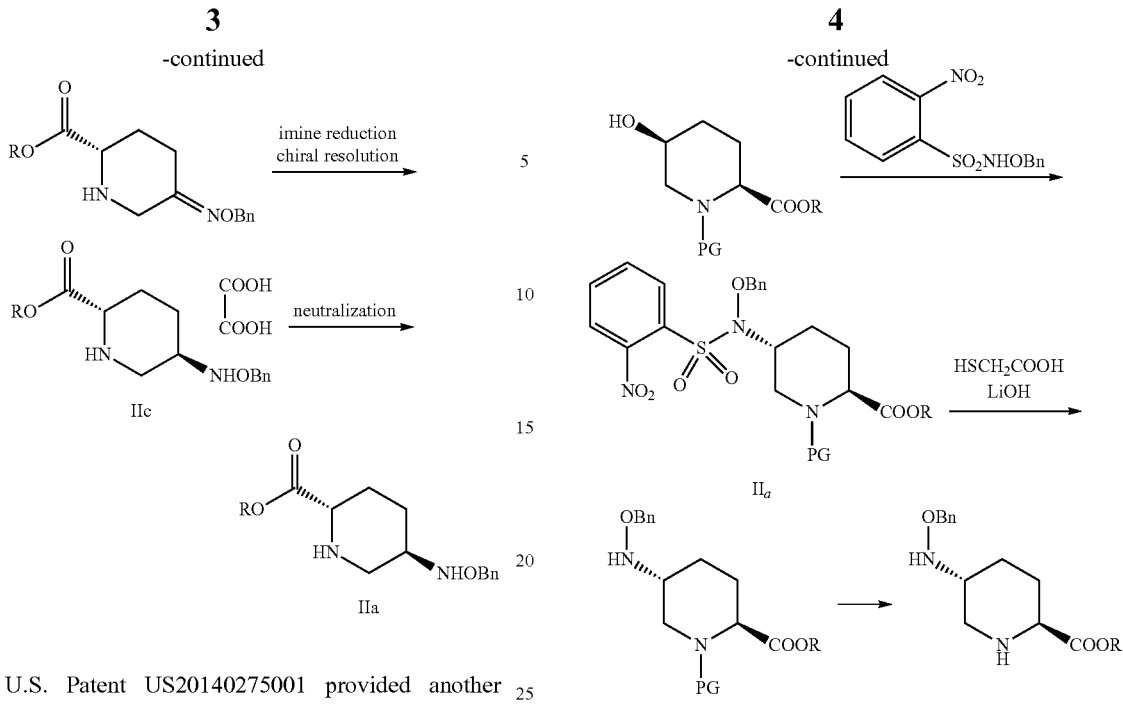

The U.S. Patent US20140275001 provided another method of synthesizing 5R-[(benzyloxy) amino] piperidine-2S-carboxylate (II$_a$) (see Scheme 2), a technical solution of which also comprised using N-protected L-pyroglutamic acid ester as the starting material and opening the ring by trimethyl sulfoxide iodide to extend carbon chain; the difference lies in that the US20140275001 first used iridium catalyst to close the ring, followed by chiral reduction of the carbonyl group to obtain an S-configuration alcohol, and then inverted the SN2 configuration by N-benzyloxy-2-nitrobenzenesulfonamide to convert the hydroxy group to amino; firstly, the 2-nitrobenzene sulfonyl chloro group was removed under the action of lithium hydroxide and mercaptoacetic acid, followed by removing the N-protecting group by trifluoroacetic acid, thereby obtaining the product II$_a$. This method has tedious operations and uses the expensive iridium catalyst and mercaptoacetic acid with a special odour; besides, it produces a large amount of wastewater with a total yield of only 15%.

Scheme 2

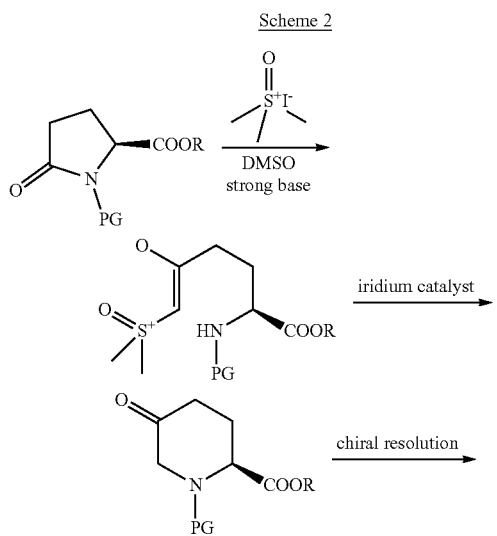

Both Scheme 1 and Scheme 2 adopt expensive starting materials and a method of extending carbon chain by trimethyl sulfoxide iodide; besides, the method of Scheme 2 uses the expensive iridium catalyst. Both reaction processes need protection and deprotection; their operations are extremely tedious and use a large amount of solvent; they have a high discharge of "wastewater, waste gas, and residuals," with a low atom utilization and being detrimental to the environment. Meanwhile, the methods in the prior art have a low product yield, which do not facilitate a green industrial production.

SUMMARY

To overcome the drawbacks in the prior art, the present application provides a green method of preparing 5R-[(benzyloxy) amino] piperidine-2S-carboxylate (II$_a$), 5R-[(benzyloxy) amino] piperidine-2S-carboxylate oxalate (II$_c$), and 5R-[(benzyloxy) amino] piperidine-2S-carboxylic acid (II$_b$), which uses an inexpensive and easily available starting material and has a simplified process and a significantly improved product yield.

Avibactam and relebactam may be prepared using the obtained 5R-[(benzyloxy) amino] piperidine-2S-carboxylate (II$_a$) or 5R-[(benzyloxy) amino] piperidine-2S-carboxylic acid (II$_b$) obtained according to the present application.

Terms:

Compound III: diester of L-glutamic acid hydrochloride (III);

Compound IV: diester of N-protecting group-N-alkoxycarbonylmethyl-L-glutamic acid (IV);

Compound V: N-protecting group piperidine-5-one-2S-carboxylate (V);

Compound VI: piperidine-5-one-2S-carboxylate (VI);

Compound VII: 5-benzyloxyiminopiperidine-2S-carboxylate (VII);

Compound VIII: N-protecting group piperidine-5-one-2S-carboxylic acid (VIII);

Compound IX: piperidine-5-one-2S-carboxylic acid (IX);

Compound X: 5-benzyloxyiminopiperidine-2S-carboxylic acid (X);
Compound XI: N-protecting group-5-benzyloxyiminopiperidine-2S-carboxylate (XI);
Compound XII: N-protecting group-5R-[(benzyloxy) amino] piperidine-2S-carboxylate (XII);
Compound IIa: 5R-[(benzyloxy) amino] piperidine-2S-carboxylate (II$_a$);
Compound IIb: 5R-[(benzyloxy) amino] piperidine-2S-carboxylic acid (II$_b$);
Compound IIc: 5R-[(benzyloxy) amino] piperidine-2S-carboxylate oxalate (II$_c$).

The numbering of the compounds in the specification is completely consistent with the numbering of their structural formulae, and they have same references.

A technical solution of the present application is provided below:

A green method of preparing 5R-[(benzyloxy) amino] piperidine-2S-carboxylate (II$_a$), 5R-[(benzyloxy) amino] piperidine-2S-carboxylate oxalate (II$_c$), and 5R-[(benzyloxy) amino] piperidine-2S-carboxylic acid (II$_b$) comprises steps of:

using L-glutamic acid as a starting material, which is first subjected to esterification reaction in the presence of an acidic reagent to prepare compound III, reacting compound III successively with 2-haloacetate and N-protecting agent, or with N-protecting agent and 2-haloacetate under a basic condition in a "one-pot" approach to obtain compound IV; subjecting the obtained compound IV to intramolecular condensation into a ring under the action of a strong base to obtain N-protecting group piperidine-5-one-2S-carboxylate (V). The obtained N-protecting group piperidine-5-one-2S-carboxylate (V) is used to prepare 5R-[(benzyloxy) amino] piperidine-2S-carboxylic acid via one of the routes below: Route 1: compound V is subjected to removal of protecting group, condensation with benzyloxyamine hydrochloride, imine reduction-chiral resolution, neutralization, and hydrolysis; Route 2: compound V is subjected to hydrolysis, removal of protecting group, condensation with benzyloxyamine hydrochloride, imine reduction-chiral resolution, and neutralization; Route 3: compound V is subjected to condensation with benzyloxyamine hydrochloride, imine reduction-chiral resolution, removal of protecting group, neutralization, and hydrolysis.

The reaction formula is provided below:

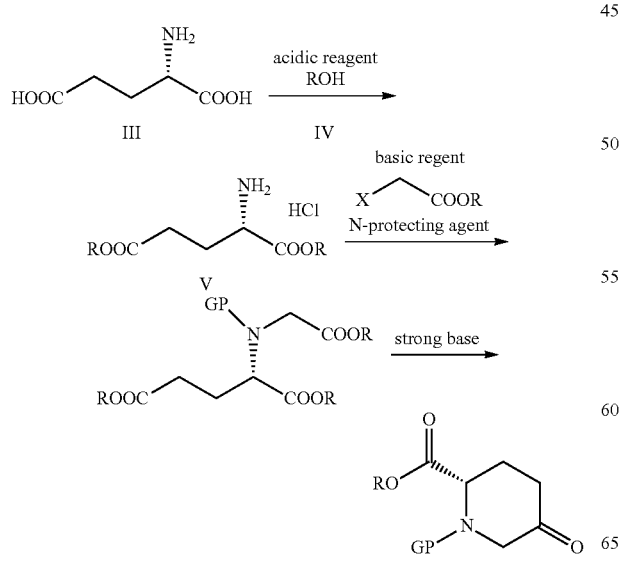

Route 1:

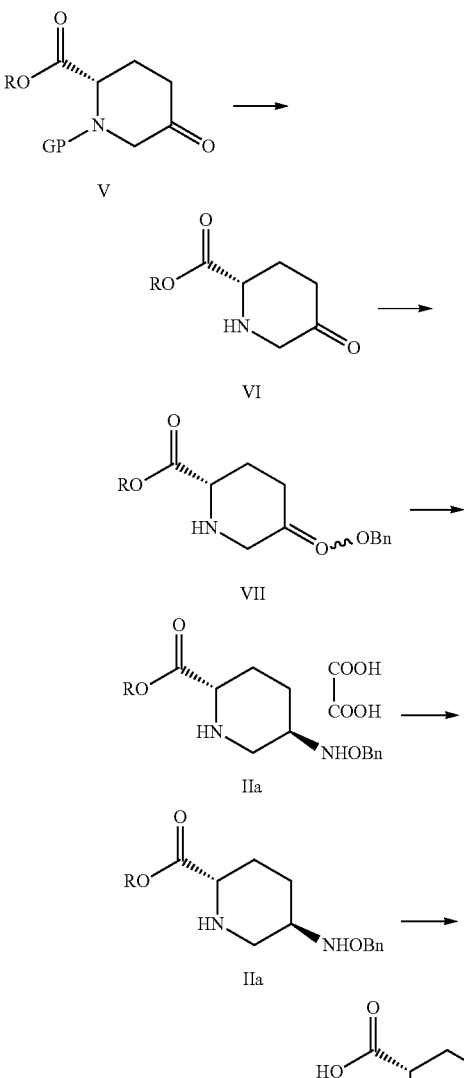

Route 2:

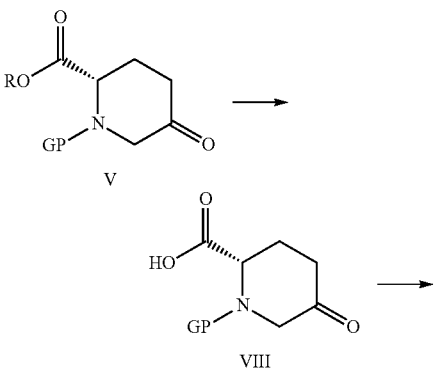

7
-continued

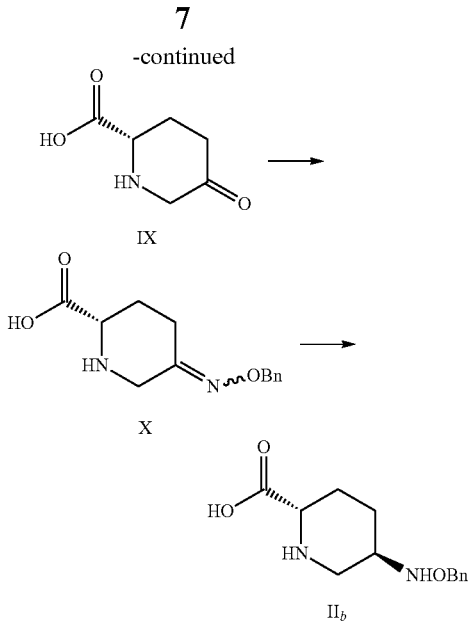

Route 3:

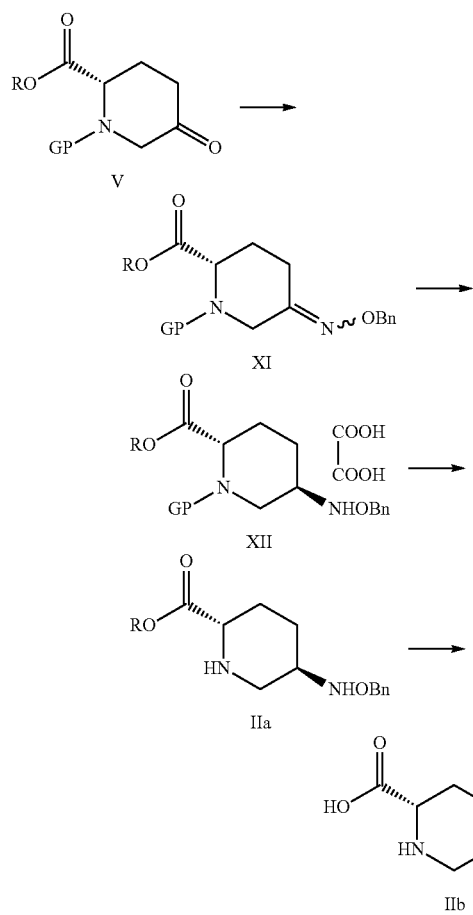

where R denotes: methyl, ethyl, n-propyl, isopropyl, tert-butyl, n-butyl, sec-butyl, benzyl PG denotes: benzyl, benzoyl, methoxycarbonyl, tert-butoxycarbonyl, benzyloxycarbonyl 8
Scheme 3

More specifically, a method of preparing 5R-[(benzyloxy) amino] piperidine-2S-carboxylic acid or a derivative thereof, wherein 5R-[(benzyloxy) amino] piperidine-2S-carboxylic acid or its derivative refers to 5R-[(benzyloxy) amino] piperidine-2S-carboxylate ($II_a$), 5R-[(benzyloxy) amino] piperidine-2S-carboxylate oxalate ($II_c$), and 5R-[(benzyloxy) amino] piperidine-2S-carboxylic acid ($II_b$), comprises the following steps.

(1) Reacting L-glutamic acid with alcohol via esterification reaction in the presence of an acidic reagent to prepare compound III, namely diester of L-glutamic acid hydrochloride.

Preferably, the acidic reagent is selected from the group consisting of thionyl chloride, phosgene, diphosgene, triphosgene, and oxalyl chloride, wherein a temperature for the esterification reaction ranges from 30° C. to 100° C.; the alcohol is selected from the group consisting of $C_{1-6}$ saturated fatty alcohol, substituted $C_{6-9}$ aromatic alcohol, or alkyl-substituted aromatic alcohol.

(2) Upon completion of step (1), distilling the reaction system to recover excess acidic reagent and alcohol, then adding the same alcohol as in step (1) to the remnant, and then successively adding a base, 2-haloacetate, and N-protecting agent, or successively adding the base, N-protecting agent, and 2-haloacetate; after twice substitution reactions, obtaining compound IV, wherein the reaction temperature preferably ranges from 20° C. to 85° C.

(3) Condensing compound IV under the action of a solvent and a strong base into a ring to obtain compound V, wherein preferably, the solvent is selected from the group consisting of tetrahydrofuran, 2-methyltetrahydrofuran, methoxycyclopentane, and toluene; a mass ratio of the solvent to compound IV is 4~20:1; a reaction temperature for the intramolecular condensation into a ring ranges from −20° C. to 50° C., and a reaction duration ranges from 2 hours to 7 hours.

A target product is prepared through one of the following routes, wherein the specific route and the corresponding steps are selected based on the target product:

Route 1:

(1.1) subjecting the obtained compound V to removal of the N-protecting group to obtain compound VI, namely piperidine-5-one-2S-carboxylate (VI);

(1.2) condensing the obtained compound VI with benzyloxyamine hydrochloride in the presence of the solvent and triethylamine to obtain compound VII, wherein preferably, the solvent is selected from the group consisting of ethyl acetate, dichloromethane, chloroform, 1,2-dichloroethane, benzene, and toluene, or a combination thereof; the reaction temperature ranges from 40° C. to 80° C.;

(1.3) subjecting the obtained compound VII to reduction by a reductant in ethyl acetate and in the presence of concentrated sulfuric acid, reacting the resultant product with added oxalate, and carrying out chiral resolution, to obtain 5R-[(benzyloxy) amino] piperidine-2S-carboxylate oxalate ($II_c$);

(1.4) neutralizing the obtained 5R-[(benzyloxy) amino] piperidine-2S-carboxylate oxalate to obtain 5R-[(benzyloxy) amino] piperidine-2S-carboxylate ($II_a$); and (1.5) subjecting the obtained 5R-[(benzyloxy) amino] piperidine-2S-carboxylate ($II_a$) to hydrolysis and acidification to obtain 5R-[(benzyloxy) amino] piperidine-2S-carboxylic acid ($II_b$);

Route 2:

(2.1) subjecting the obtained compound V to hydrolysis of ester group to obtain compound VIII, namely N-protecting group piperidine-5-one-2S-carboxylic acid (VIII);

(2.2) subjecting compound VIII, namely, N-protecting group piperidine-5-one-2S-carboxylic acid, to removal of N-protecting group, to obtain compound IX, namely piperidine-5-one-2S-carboxylic acid (IX);

(2.3) condensing the obtained compound IX, namely piperidine-5-one-2S-carboxylic acid (IX), with benzyloxyamine hydrochloride in the presence of the solvent and triethylamine to obtain compound X, namely 5-benzyloxyiminopiperidine-2S-carboxylic acid (X), wherein preferably, the solvent is selected from the group consisting of ethyl acetate, dichloromethane, chloroform, 1,2-dichloroethane, benzene and toluene, or a combination thereof; the reaction temperature ranges from 40° C. to 80° C.;

(2.4) subjecting the obtained compound X to reduction with a reductant in ethyl acetate and in the presence of concentrated sulfuric acid, reacting the resultant product with added oxalate, carrying out chiral resolution and neutralization, to obtain 5R-[(benzyloxy) amino] piperidine-2S-carboxylic acid ($II_b$).

Route 3:

(3.1) condensing the obtained compound V with benzyloxyamine hydrochloride in the presence of the solvent and triethylamine to obtain compound XI, namely N-protecting group-5-benzyloxyiminopiperidine-2S-carboxylate (XI), wherein preferably, the solvent is selected from the group consisting of ethyl acetate, dichloromethane, chloroform, 1,2-dichloroethane, benzene and toluene, or a combination thereof; the reaction temperature ranges from 40° C. to 80° C.;

(3.2) subjecting the obtained compound XI to reduction with a reductant in ethyl acetate and in the presence of concentrated sulfuric acid, reacting the resultant product with added oxalate, and carrying out chiral resolution, to obtain compound XII, namely, N-protecting group-5R-[(benzyloxy) amino] piperidine-2S-carboxylate (XII);

(3.3) subjecting the obtained compound XII to removal of N-protecting group and neutralization to obtain 5R-[(benzyloxy) amino] piperidine-2S-carboxylate ($II_a$);

(3.4) subjecting the obtained 5R-[(benzyloxy) amino] piperidine-2S-carboxylate ($II_a$) to hydrolysis and acidification to obtain 5R-[(benzyloxy) amino] piperidine-2S-carboxylic acid ($II_b$).

According to the present application, in step (1), when the acidic reagent is thionyl chloride or phosgene, a molar ratio of thionyl chloride or phosgene to L-glutamic acid is (2.1-4.5): 1, wherein preferably a temperature for the esterification reaction ranges from 40° C. to 80° C., and a reaction duration ranges from 1 hour to 8 hours; when the acidic reagent is diphosgene or oxalyl chloride, a molar ratio of diphosgene or oxalyl chloride to L-glutamic acid is (1.1-2.5): 1, wherein preferably the temperature for the esterification reaction ranges from 40° C. to 80° C., and the reaction duration ranges from 1 hour to 8 hours; when the acidic reagent is triphosgene, the molar ratio of triphosgene to L-glutamic acid is (0.7-1.5): 1, wherein preferably the temperature for the esterification reaction ranges from 60° C. to 80° C., and the reaction duration ranges from 1 hour to 8 hours.

Preferably, according to the present application, in step (1), a mass ratio of the alcohol to L-glutamic acid ranges from 8:1 to 30:1. The $C_{1-6}$ saturated fatty alcohol is selected from the group consisting of methanol, ethanol, n-propanol, isopropanol, n-butanol, isobutanol, tert-butanol, n-pentanol, isoamyl alcohol, tert-amyl alcohol, and hexyl alcohol; and the substituted $C_{6-9}$ aromatic alcohol or alkyl-substituted aromatic alcohol is selected from the group consisting of benzyl alcohol, o-methylbenzyl alcohol, and p-methylbenzyl alcohol.

In step (2), the alcohol same as that added in step (1) refers to an alcohol of the same kind and quality.

Preferably, according to the present application, the base in step (2) refers to an inorganic base or an organic base, wherein the inorganic base is selected from the group consisting of potassium carbonate, sodium carbonate, calcium carbonate, potassium bicarbonate, sodium bicarbonate, calcium bicarbonate, potassium acetate, sodium acetate, and calcium acetate, or a combination thereof, and the organic base is selected from the group consisting of trimethylamine, triethylamine, and tri-n-butylamine, or a combination thereof;

Preferably, according to the present application, in step (2), the 2-haloacetate is selected from the group consisting of methyl 2-chloroacetate, methyl 2-bromoacetate, methyl 2-iodoacetate, methyl 2-iodoacetate, ethyl 2-chloroacetate, ethyl 2-bromoacetate, ethyl 2-iodoacetate, ethyl 2-iodoacetate, benzyl 2-chloroacetate, benzyl 2-bromoacetate, benzyl 2-iodoacetate, and benzyl 2-iodoacetate.

Preferably, according to the present application, in step (2), the N-protecting agent is selected from the group consisting of benzyl chloride, benzyl bromide, benzoyl chloride, methyl chloroformate, ethyl chloroformate, tert-butyl chloroformate, benzyl chloroformate, 9-fluorenylmethyl chloroformate, and di-tert-butyl dicarbonate.

Preferably, according to the present application, in step (2), the molar ratios of the 2-haloacetate, the N-protecting agent, the base and L-glutamic acid are (1.0-2.0):(1.0-2.0):(2.0-4.0): 1, respectively; preferably, the reaction temperature ranges from 40° C. to 70° C., and a duration of the two substitution reactions both ranges from 1 hour to 5 hours.

Preferably, according to the present application, in step (3), the strong base is selected from the group consisting of sodium hydride, sodium methoxide, sodium ethoxide, sodium tert-butoxide, potassium tert-butoxide or sodium benzylate; further preferably, a molar ratio of the strong base to compound IV is (1.0-2.0):1.

Preferably, according to the present application, the detailed steps of Route 1 are provided below:

Preferably, according to the present application, the step (1.1) of subjecting the obtained compound V to removal of the N-protecting group to obtain compound VI is performed in one of the following manners based on different N-protecting groups: when the N-protecting group is benzyl, debenzylation is performed using catalytic hydrogenolysis; when the N-protecting group is benzoyl or alkoxycarbonyl, the corresponding N-protecting group is removed by hydrolysis under a basic condition; preferably, the catalyst used in the catalytic hydrogenolysis in step (1.1) is palladium on carbon or Raney nickel, and preferably, amount of the palladium on carbon catalyst is 0.5%~5% of the mass of compound V, and further preferably, the amount of the catalyst is 1%~3% by mass; preferably, amount of the Raney nickel is 1%~20% of the mass of compound V, and further preferably the amount of the catalyst is 5%~10% by mass. Preferably, the solvent in step (1.1) is selected from the group consisting of methanol, ethanol, propanol, butanol, ethyl acetate, tetrahydrofuran, and acetonitrile, or a mixed solvent thereof, and further preferably, a mass ratio of the solvent to compound V ranges from 4:1 to 15:1; preferably, in step (1.1), a hydrogen pressure ranges from 0.1 Mpa to 1.0 MPa, a reaction temperature ranges from 20° C. to 85° C., and a reaction duration ranges from 3 hours to 10 hours. When the N-protecting group is benzoyl or alkoxycarbonyl, the corresponding N-protecting group is removed by hydrolysis under a basic condition; preferably, in step (1.1), the base is selected from the group consisting of potassium hydroxide, sodium hydroxide, and lithium hydroxide; a molar ratio of the base to compound V is (2.0-3.0):1; preferably, the solvent in step (1.1) is selected from the group consisting of water, methanol, ethanol, propanol, butanol, ethyl acetate, tetrahydrofuran, and acetonitrile, or a mixed solvent thereof, and further preferably, a mass ratio of the solvent to compound V ranges from 3:1 to 15:1; preferably, a temperature for the hydrolysis reaction in step (1.1) ranges from 10° C. to 100° C., and a reaction duration ranges from 2 hours to 10 hours.

Preferably, according to the present application, the solvent in step (1.2) is selected from the group consisting of methanol, ethanol, propanol, butanol, ethyl acetate, tetrahydrofuran, and acetonitrile, or a mixed solvent thereof, and further preferably, a mass ratio of the solvent to compound VI ranges from 3:1 to 15:1.

Preferably, according to the present application, in step (1.2), a molar ratio of benzyloxyamine hydrochloride and compound VI ranges from 0.9:1 to 1.5:1; wherein preferably the reaction temperature ranges from 10° C. to 80° C., and the reaction duration ranges from 2 hours to 5 hours.

Preferably, according to the present application, in step (1.3), the concentrated sulfuric acid is a sulfuric acid with a mass fraction of 95%~98%, a molar ratio of the concentrated sulfuric acid to compound VII ranges from 3.0:1 to 6.0:1, and preferably, the concentrated sulfuric acid is a sulfuric acid with a mass fraction of 98%.

Preferably, according to the present application, in step (1.3), a mass ratio between ethyl acetate and compound VII is 5-20:1; further preferably, the mass ratio between ethyl acetate and compound VII ranges from 10-14:1.

Preferably, according to the present application, in step (1.3), the reductant is selected from the group consisting of sodium borohydride, sodium tricyanoborohydride, sodium triacetoxyborohydride, sodium tripropionyloxy borohydride, potassium borohydride, potassium tricyanoborohydride, potassium triacetoxyborohydride and potassium tripropionyloxy borohydride. A molar ratio of the reductant to compound VII is (2.0-4.0): 1.

Preferably, according to the present application, in step (1.4), the obtained 5R-[(benzyloxy) amino] piperidine-2S-carboxylate oxalate is neutralized with a base in the solvent to obtain 5R-[(benzyloxy) amino] piperidine-2S-carboxylate ($II_a$).

Preferably, according to the present application, in step (1.4), the solvent is selected from the group consisting of ethyl acetate, dichloromethane, chloroform, 1,2-dichloroethane, benzene, and methylbenzene, or a mixture thereof; preferably, a mass ratio of the solvent to compound IIb ranges from 4:1 to 12:1.

Preferably, according to the present application, in step (1.4), the base is selected from the group consisting of potassium carbonate, sodium carbonate, calcium carbonate, potassium bicarbonate, sodium bicarbonate, calcium bicarbonate, and ammonium hydroxide or a combination thereof; preferably, the molar ratio of the base to 5R-[(benzyloxy) amino] piperidine-2S-carboxylate oxalate is (1.5-3.0):1.

Preferably, according to the present application, in step (1.4), a temperature for the neutralization reaction ranges from 10° C. to 40° C., and a reaction duration ranges from 2 hours to 5 hours.

Preferably, according to the present application, in step (1.5), the obtained 5R-[(benzyloxy) amino] piperidine-2S-carboxylate ($II_a$) is subjected to hydrolysis with a base in the solvent to obtain 5R-[(benzyloxy) amino] piperidine-2S-carboxylic acid ($II_b$).

Preferably, according to the present application, in step (1.5), the solvent is selected from the group consisting of water, ethyl acetate, dichloromethane, chloroform, 1,2-dichloroethane, benzene, and methylbenzene, or a mixture thereof; preferably, a mass ratio of the solvent to compound IIa ranges from 4:1 to 12:1.

Preferably, according to the present application, in step (1.5), the base is selected from the group consisting of sodium hydroxide, potassium hydroxide, lithium hydroxide, potassium carbonate, sodium carbonate, calcium carbonate, potassium bicarbonate, and sodium bicarbonate, or a combination thereof; preferably, a molar ratio of the base to 5R-[(benzyloxy) amino] piperidine-2S-carboxylate (IIa) is (1.5-3.0):1.

Preferably, according to the present application, in step (1.5), a temperature for the hydrolysis reaction ranges from 10° C. to 80° C., and a reaction duration ranges from 2 hours to 5 hours.

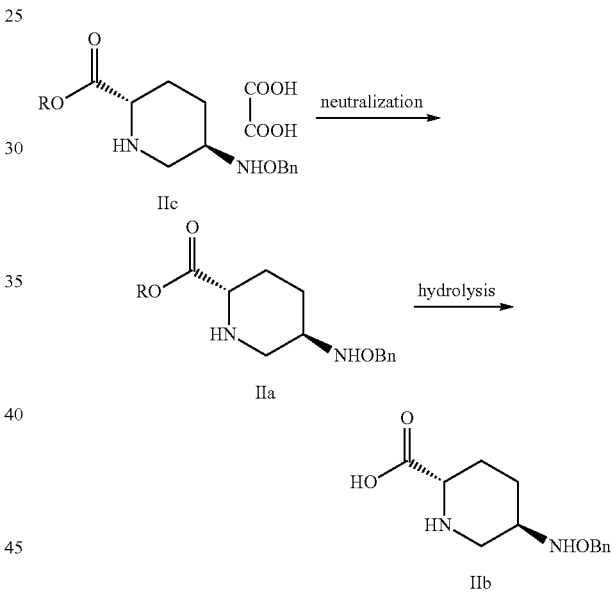

Preferably, according to the present application, the detailed steps of Route 2 are provided below.

Preferably, according to the present application, in step (2.1), compound V is hydrolyzed by a base in a solvent to obtain compound VIII, namely N-protecting group piperidine-5-one-2S-carboxylic acid (VIII).

Preferably, according to the present application, in step (2.1), the solvent is selected from the group consisting of water, ethyl acetate, dichloromethane, chloroform, 1,2-dichloroethane, benzene, and toluene, or a mixture thereof; preferably, a mass ratio of the solvent to compound V ranges from 4:1 to 12:1.

Preferably, according to the present application, in step (2.1), the base is selected from the group consisting of sodium hydroxide, potassium hydroxide, lithium hydroxide, potassium carbonate, sodium carbonate, calcium carbonate, potassium bicarbonate, and sodium bicarbonate, or a combination thereof; preferably, a molar ratio of the base to compound V is (1.5-3.0):1.

Preferably, according to the present application, in step (2.1), a temperature for the hydrolysis reaction ranges from 10° C. to 80° C., and a reaction duration ranges from 2 hours to 5 hours.

Preferably, according to the present application, in step (2.2), the obtained compound VIII is subjected to removal of the N-protecting group to obtain compound IX, namely, piperidine-5-one-2S-carboxylic acid (IX); removal of the N-protecting group is performed in the following manner based on different N-protecting groups: when the N-protecting group is benzyl, debenzylation is performed by catalytic hydrogenolysis; when the N-protecting group is benzoyl or alkoxycarbonyl, the corresponding N-protecting group is removed by hydrolysis under a basic condition; preferably, the catalyst used in the catalytic hydrogenolysis in step (2.2) is palladium on carbon or Raney nickel, and preferably, amount of the palladium on carbon catalyst is 0.5%~5% of the mass of compound VIII, and further preferably, the amount of the catalyst is 1%~3% by mass; preferably, amount of the Raney nickel is 1%~20% of the mass of compound VIII, and further preferably the amount of the catalyst is 5%~10% by mass. Preferably, the solvent in step (1.1) is selected from the group consisting of methanol, ethanol, propanol, butanol, ethyl acetate, tetrahydrofuran, and acetonitrile, or a mixed solvent thereof, and further preferably, a mass ratio of the solvent to compound VIII ranges from 4:1 to 15:1; preferably, in step (1.1), a hydrogen pressure ranges from 0.1 Mpa to 1.0 MPa, a reaction temperature ranges from 20° C. to 85° C., and a reaction duration ranges from 3 hours to 10 hours. When the N-protecting group is benzoyl or alkoxycarbonyl, the corresponding N-protecting group is removed by hydrolysis under a basic condition; preferably, in step (1.1), the base is selected from the group consisting of potassium hydroxide, sodium hydroxide, and lithium hydroxide; a molar ratio of the base to compound VIII is (2.0-3.0):1; preferably, the solvent in step (1.1) is selected from the group consisting of water, methanol, ethanol, propanol, butanol, ethyl acetate, tetrahydrofuran, and acetonitrile, or a mixed solvent thereof, and further preferably, a mass ratio of the solvent to compound VIII ranges from 3:1 to 15:1; preferably, a temperature for the hydrolysis reaction in step (1.1) ranges from 10° C. to 100° C., and a reaction duration ranges from 2 hours to 10 hours.

Preferably, according to the present application, in step (2.3), the solvent is selected from the group consisting of methanol, ethanol, propanol, butanol, ethyl acetate, tetrahydrofuran, and acetonitrile, or a mixed solvent thereof, and further preferably, a mass ratio of the solvent to compound IX ranges from 3:1 to 15:1.

Preferably, according to the present application, in step (2.3), a molar ratio of benzyloxyamine hydrochloride to compound IX ranges from 0.9:1 to 1.5:1, wherein preferably the reaction temperature ranges from 10° C. to 80° C., and the reaction duration ranges from 2 hours to 5 hours.

Preferably, according to the present application, in step (2.4), the concentrated sulfuric acid is a sulfuric acid with a mass fraction of 95%~98%, a molar ratio between the concentrated sulfuric acid and compound X ranges from 3.0:1 to 6.0:1, and most preferably, the concentrated sulfuric acid is a sulfuric acid with a mass fraction of 98%.

Preferably, according to the present application, in step (2.4), a mass ratio of ethyl acetate to compound X is 5-20:1; further preferably, the mass ratio of ethyl acetate to compound X ranges from 10-14:1.

Preferably, according to the present application, in step (2.4), the reductant is selected from the group consisting of sodium borohydride, sodium tricyanoborohydride, sodium triacetoxyborohydride, sodium tripropionyloxy borohydride, potassium borohydride, potassium tricyanoborohydride, potassium triacetoxyborohydride and potassium tripropionyloxy borohydride. A molar ratio between the reductant and compound X is (2.0-4.0): 1.

Preferably, according to the present application, the detailed steps of Route 3 are provided below.

Preferably, according to the present application, in step (3.1), the obtained compound V is condensed with benzyloxyamine hydrochloride in the presence of a solvent and a base to obtain compound XI, namely N-protecting group-5-benzyloxyiminopiperidine-2S-carboxylate (XI).

Preferably, according to the present application, in step (3.1), the solvent is selected from the group consisting of methanol, ethanol, propanol, butanol, ethyl acetate, tetrahydrofuran, acetonitrile, dichloromethane, chloroform, 1,2-dichloroethane, benzene, and toluene, or a mixture thereof, and further preferably, a mass ratio of the solvent to compound V ranges from 3:1 to 15:1.

Preferably, according to the present application, in step (3.1), the base is selected from the group consisting of triethylamine, tri-n-butylamine, diisopropylethylamine, and piperidine, which are organic bases, and potassium carbonate, sodium carbonate, which are inorganic bases, or a mixture thereof, and a molar ratio of the base to compound V is (1.0-2.0):1.

Preferably, according to the present application, in step (3.1), a molar ratio of benzyloxyamine hydrochloride to compound V is 0.9-1.5:1; preferably, the reaction temperature ranges from 10° C. to 80° C., and the reaction duration ranges from 2 hours to 5 hours.

Preferably, according to the present application, in step (3.2), compound XI is subjected to reduction by a reductant in ethyl acetate and in the presence of concentrated sulfuric acid, reaction with added oxalate, and chiral resolution to obtain compound XII, namely, N-protecting group-5R-[(benzyloxy) amino] piperidine-2S-carboxylate (XII).

Preferably, according to the present application, in step (3.2), the concentrated sulfuric acid is a sulfuric acid with a mass fraction of 95%~98%, a molar ratio between the concentrated sulfuric acid and compound XI ranges from 3.0:1 to 6.0:1, and most preferably, the concentrated sulfuric acid is a sulfuric acid with a mass fraction of 98%.

Preferably, according to the present application, in step (3.2), a mass ratio of ethyl acetate to compound XI is 5-20:1; further preferably, the mass ratio of ethyl acetate to compound XI is 10-14:1.

Preferably, according to the present application, in step (3.2), the reductant is selected from the group consisting of sodium borohydride, sodium tricyanoborohydride, sodium triacetoxyborohydride, sodium tripropionyloxy borohydride, potassium borohydride, potassium tricyanoborohydride, potassium triacetoxyborohydride and potassium tripropionyloxy borohydride. A molar ratio of the reductant to compound XI is (2.0-4.0): 1.

Preferably, according to the present application, in step (3.3), compound XII is subjected to removal of the N-protecting group and neutralization to obtain compound 5R-[(benzyloxy) amino] piperidine-2S-carboxylate ($II_a$).

Preferably, according to the present application, in the step (3.3) of subjecting compound XII to removal of the N-protecting group and neutralization to obtain compound $II_a$, and dependent on different N-protecting groups, one of the following manners is selected to remove the respective N-protecting group: when the N-protecting group is benzyl, debenzylation is performed using catalytic hydrogenolysis;

when the N-protecting group is benzoyl or alkoxycarbonyl, the corresponding N-protecting group is removed by hydrolysis under a basic condition; preferably, the catalyst used in the catalytic hydrogenolysis in step (3.3) is palladium on carbon or Raney nickel, and preferably, amount of the palladium on carbon catalyst is 0.5%~5% of the mass of compound XII and further preferably, the amount of the catalyst is 1%~3% by mass; preferably, amount of the Raney nickel catalyst is 1%~20% of the mass of compound XII, and further preferably the amount of the catalyst is 5%~10% by mass. Preferably, the solvent in step (3.3) is selected from the group consisting of methanol, ethanol, propanol, butanol, ethyl acetate, tetrahydrofuran, and acetonitrile, or a mixed solvent thereof, and further preferably, a mass ratio of the solvent to compound XII ranges from 4:1 to 15:1; preferably, in step (3.3), a hydrogen pressure ranges from 0.1 Mpa to 1.0 MPa, a reaction temperature ranges from 20° C. to 85° C., and the total duration of deprotection and neutralization ranges from 3 hours to 10 hours. When the N-protecting group is benzoyl or alkoxycarbonyl, the corresponding N-protecting group is removed by hydrolysis under a basic condition; preferably, in step (3.3), the base is selected from the group consisting of potassium hydroxide, sodium hydroxide, and lithium hydroxide; a molar ratio of the base to compound XII is (2.0-3.0):1; preferably, the solvent in step (3.3) is selected from the group consisting of water, methanol, ethanol, propanol, butanol, ethyl acetate, tetrahydrofuran, and acetonitrile, or a mixed solvent thereof, and further preferably, a mass ratio of the solvent to compound XII ranges from 3:1 to 15:1; preferably, a temperature for the hydrolysis reaction in step (1.1) ranges from 10° C. to 100° C., and a reaction duration ranges from 2 hours to 10 hours.

Preferably, according to the present application, in step (3.4), the obtained 5R-[(benzyloxy) amino] piperidine-2S-carboxylate ($II_a$) is subjected to hydrolysis and acidification to obtain 5R-[(benzyloxy) amino] piperidine-2S-carboxylic acid ($II_b$).

Preferably, according to the present application, in step (3.4), the solvent is selected from the group consisting of water, ethyl acetate, dichloromethane, chloroform, 1,2-dichloroethane, benzene, and toluene, or a mixture thereof; preferably, a mass ratio of the solvent to compound IIa ranges from 4:1 to 12:1.

Preferably, according to the present application, in step (3.4), the base is selected from the group consisting of sodium hydroxide, potassium hydroxide, lithium hydroxide, potassium carbonate, sodium carbonate, calcium carbonate, potassium bicarbonate, and sodium bicarbonate, or a combination thereof; preferably, a molar ratio of the base to compound IIa is (1.5-3.0):1.

Preferably, according to the present application, in step (3.4), a temperature for the hydrolysis reaction ranges from 10° C. to 80° C., and a reaction duration ranges from 2 hours to 5 hours.

A target product is prepared by selecting a corresponding route dependent on a specific target product and a specific protecting group.

The avibactam ($I_a$) and relebactam ($I_b$) may be prepared according to the existing methods by using 5R-[(benzyloxy) amino] piperidine-2S-carboxylate oxalate ($II_c$), 5R-[(benzyloxy) amino] piperidine-2S-carboxylate ($II_a$), or 5R-[(benzyloxy) amino] piperidine-2S-carboxylic acid ($II_b$) prepared according to the present application as the starting material. With 5R-[(benzyloxy) amino] piperidine-2S-carboxylate as the example, the general formula of the reaction is provided below (see Scheme 4):

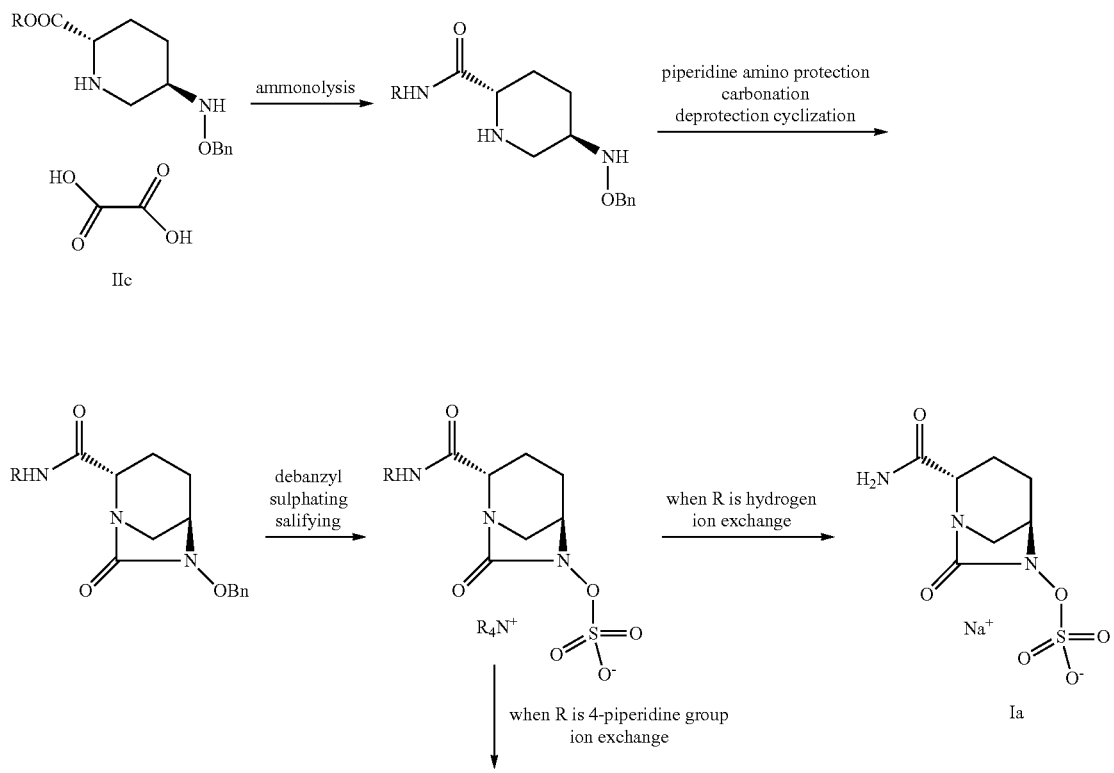

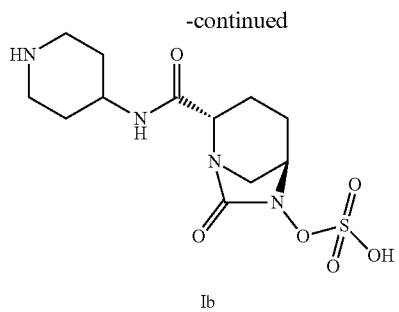

Ib

Technical Characteristics and Advantageous Effects of the Present Application:

1. The present application relates to a green method of preparing 5R-[(benzyloxy) amino] piperidine-2S-carboxylate ($II_a$), 5R-[(benzyloxy) amino] piperidine-2S-carboxylate oxalate ($II_c$), and 5R-[(benzyloxy) amino] piperidine-2S-carboxylic acid ($II_b$). The present application provides novel methods of preparing 5R-[(benzyloxy) amino] piperidine-2S-carboxylic acid and a derivative thereof; where the inexpensive and easily accessible L-glutamic acid is used as the starting material; the reaction types involved in respective steps are classical; the reaction conditions are easily controllable; the operability is strong; the process is simplified; the atomic economy is high; the total yield may reach 60.0% above, 1.5~4 times higher than the prior art; and the resulting products have a high purity, but a low cost.

2. Compared with the prior art, the solvent used in the present method is easily recyclable, with less waste liquid discharge; thus, the process is green and environment-friendly.

3. Avibactam ($I_a$) and relebactam ($I_b$) may be prepared from 5R-[(benzyloxy) amino] piperidine-2S-carboxylate ($II_a$), 5R-[(benzyloxy) amino] piperidine-2S-carboxylate oxalate ($II_c$), and 5R-[(benzyloxy) amino] piperidine-2S-carboxylic acid ($II_b$) prepared according to the present application.

DETAILED DESCRIPTION OF EMBODIMENTS

Figure 1:
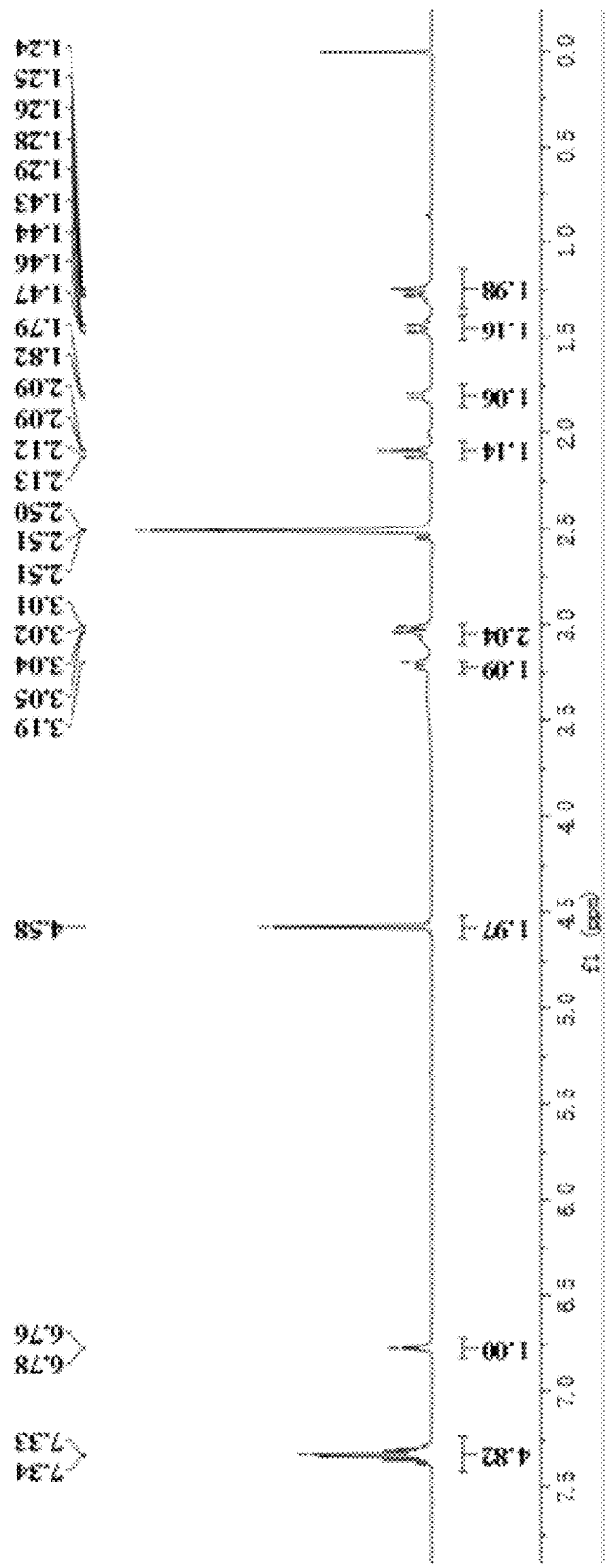
FIG. 1 shows $^1$H-NMR spectroscopy of the product prepared in Example 18 of the present application.
Figure 2:
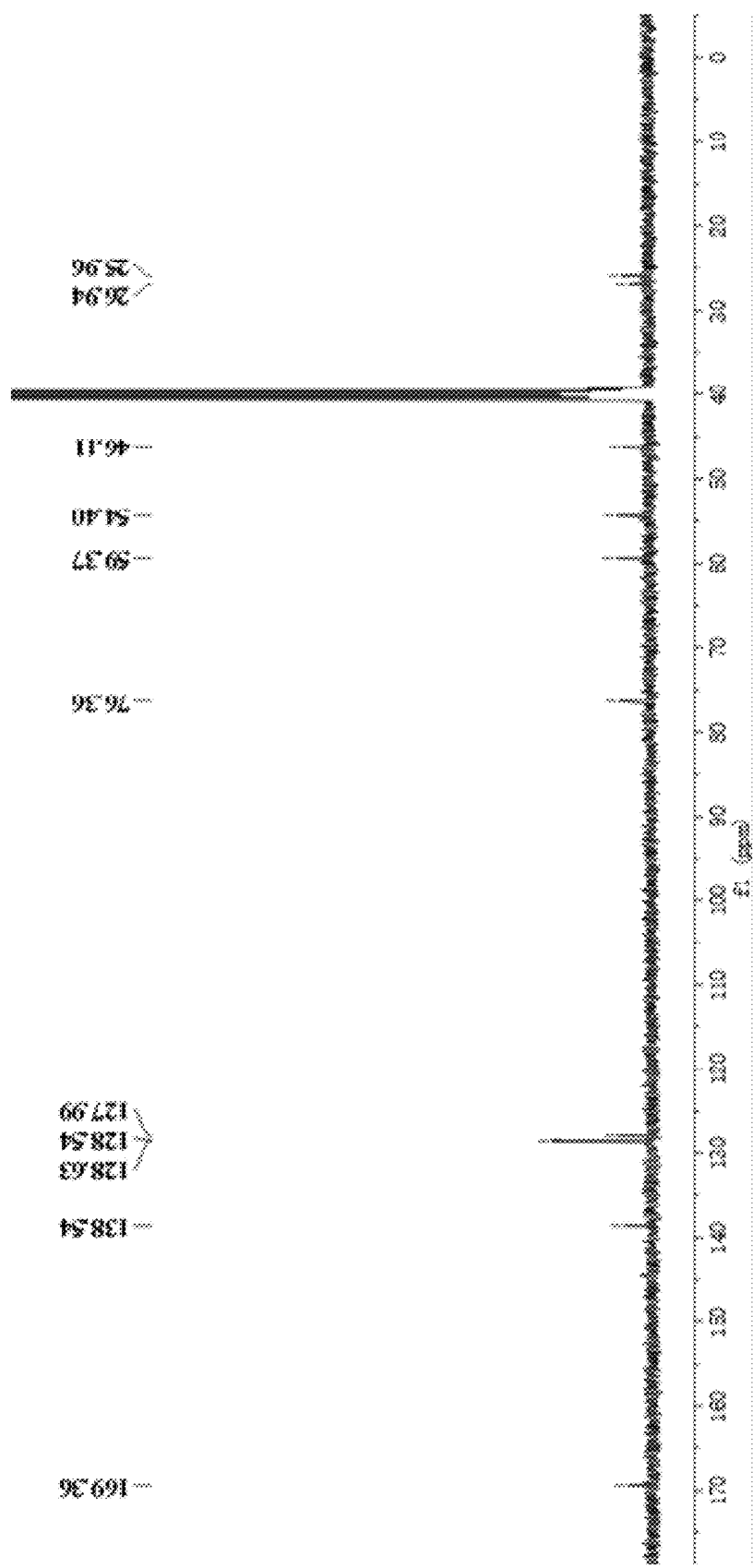
FIG. 2 shows $^1$H-NMR spectroscopy of the product prepared in Example 18 of the present application.

Hereinafter, the present application will be illustrated in detail with reference to the examples; however, the present application is not limited thereto. Based on the examples of the present application, any non-inventive solution or example derived by those skilled in the art from the present technical solution or any non-inventive change of implementation sequence of the present technical solution, falls within the protection scope of the present application.

The percentages in the examples all refer to mass percentages, unless otherwise indicated.

The reaction process and product purity are monitored by a gas chromatograph or a liquid chromatograph. A liquid chromatograph equipped with a chiral column (ES-OVS, 150 mm×4.6 mm, Agilent) is used to detect the optical purity (area ratio %) and calculate the yield and e.e % value.

Example 1: Preparation of Dimethyl N-Benzyl-N-Methoxy Carbonylmethyl-L-Glutamate ($IV_1$)

To a 500 ml 4-neck flask equipped with a stirrer, a thermometer, and a reflex condenser (connected to a 30% sodium hydroxide aqueous solution adsorption device) were charged 300 g of methanol, 14.7 g (0.10 mol) of L-glutamic acid, 30.0 g (0.25 mol) of thionyl chloride, and then heated for reaction at 60° C. to 63° C. for 7 hours, and cooled to 20° C. to 25° C. After hydrogen chloride in the system was replaced by nitrogen for 30 minutes, the reaction system was distilled to recover excess thionyl chloride and methanol, and then 300 g of fresh methanol was added to the remnants. Next, 41.5 g (0.30 mol) of potassium carbonate and 11.0 g of (0.10 mol) methyl 2-chloroacetate were charged, and the mixture was stirred to react for 4 hours at 40° C. to 45° C., and then 13.0 g (0.10 mol) of benzyl chloride was charged and stirred to react at 40° C. to 45° C. for 4 hours. After completion of the reaction without cooling, filtration was immediately carried out. The filter cake was washed twice by methanol (50 g each); after the filtrates were combined and distilled to recover methanol at a normal pressure, they were distilled at a reduced pressure to obtain 31.2 g of dimethyl N-benzyl-N-methoxycarbonylmethyl-L-glutamate as colorless and transparent liquid in a GC purity of 99.6% and a yield of 92.6%.

Example 2: Preparation of Diethyl N-Benzyl-N-Ethoxycarbonylmethyl-L-Glutamate ($Iv_2$)

To a 500 ml 4-neck flask equipped with a stirrer, a thermometer, and a reflex condenser (connected to a 30% sodium hydroxide aqueous solution adsorption device) were charged 300 g of ethanol, 14.7 g (0.10 mol) of L-glutamic acid, 25.0 g (0.08 mol) of solid phosgene, and then heated for reaction at 70° C. to 75° C. for 5 hours, and cooled to 20° C. to 25° C. After hydrogen chloride in the system was replaced by nitrogen for 30 minutes, the reaction system was distilled to recover excess triphosgene and ethanol, and then 300 g of fresh ethanol was added to the remnants. Next, 41.5 g (0.30 mol) of potassium carbonate and 17.5 g (0.10 mol) of benzyl bromide were charged, and the mixture was stirred to react at 30° C. to 35° C. for 4 hours, and then 18.5 g (0.11 mol) of ethyl 2-bromoacetate was charged and stirred to react at 40° C. to 45° C. for 4 hours. After completion of the reaction without cooling, filtration was immediately carried out. The filter cake was washed twice by ethanol (50 g each); after the filtrates were combined and distilled to recover ethanol at a normal pressure, they were distilled at a reduced pressure to obtain 36.0 g of diethyl N-benzyl-N-ethoxycarbonylmethyl-L-glutamate as colorless and transparent liquid in a GC purity of 99.8% and a yield of 95.0%.

Example 3: Preparation of Dibenzyl N-Benzyl-N-Benzyloxycarbonylmethyl-L glutamate ($IV_3$)

To a 500 ml 4-neck flask equipped with a stirrer, a thermometer, and a reflex condenser (connected to a 30% sodium hydroxide aqueous solution adsorption device) were charged 280 g of benzyl alcohol, 14.7 g (0.10 mol) of L-glutamic acid, 36.0 g (0.30 mol) of thionyl chloride, and then heated for reaction at 80° C. to 85° C. for 5 hours, and cooled to 20° C. to 25° C. After hydrogen chloride in the system was replaced by nitrogen for 30 minutes, the reaction system was distilled to recover excess thionyl chloride and benzyl alcohol, and then 280 g of fresh benzyl alcohol was added to the remnants. Next, 41.5 g (0.30 mol) of potassium carbonate and 19.5 g (0.11 mol) of benzyl 2-chloroacetate was charged, and the mixture was stirred to react at 50° C. to 55° C. for 4 hours, and then 17.5 g (0.10 mol) of benzyl bromide was charged and stirred to react at 40° C. to 45° C. for 4 hours. After completion of the reaction without cooling, filtration was immediately carried out. The filter cake was washed twice by benzyl alcohol (80 g each); after the filtrates were combined and distilled to recover benzyl alcohol at a normal pressure, they were distilled at a reduced pressure to obtain 53.5 g of dibenzyl N-benzyl-N-benzyloxycarbonylmethyl-L-glutamate as yellowish and transparent liquid in a GC purity of 99.5% and a yield of 94.7%.

Example 4: Preparation of Dimethyl N-Benzoyl-N-Methoxy Carbonyl Methyl-L-Glutamate ($IV_4$)

To a 500 ml 4-neck flask equipped with a stirrer, a thermometer, and a reflex condenser (connected to a 30% sodium hydroxide aqueous solution adsorption device) were charged 300 g of methanol, 14.7 g (0.10 mol) of L-glutamic acid, 35.0 g (0.23 mol) of thionyl chloride, and then heated for reaction at 60° C. to 63° C. for 7 hours, and cooled to 20° C. to 25° C. After hydrogen chloride in the system was replaced by nitrogen for 30 minutes, the reaction system was distilled to recover excess thionyl chloride and methanol, and then 300 g of fresh methanol was added to the remnants. Next, 41.5 g (0.30 mol) of potassium carbonate and 11.0 g (0.10 mol) of methyl 2-chloroacetate were charged, and the mixture was stirred to react at 40° C. to 45° C. for 4 hours, and then 15.0 g (0.10 mol) of benzoyl chloride was charged and stirred to react at 40° C. to 45° C. for 5 hours. After completion of the reaction without cooling, filtration was immediately carried out. The filter cake was washed twice by methanol (50 g each); after the filtrates were combined and distilled to recover methanol at a normal pressure, they were distilled at a reduced pressure to obtain 32.1 g of dimethyl N-benzoyl-N-methoxy carbonyl methyl-L-glutamate as yellowish and transparent liquid in a GC purity of 99.5% and a yield of 91.5%.

Example 5: Preparation of Methyl N-benzylpiperidine-5-one-2S-carboxylate ($V_1$)

To a 500 ml 4-neck flask equipped with a stirrer and a thermometer were charged 200 g of tetrahydrofuran, 6.0 g (0.11 mol) of sodium methoxide, cooled to −5° C. to 0° C., and then added dropwise with 33.7 g (0.10 mol) of dimethyl N-benzyl-N-methoxy carbonyl methyl-L-glutamate (prepared in Example 1) at that temperature; after completion of the dropwise adding, the mixture was stirred to react at 20° C. to 25° C. for 4 hours, and then filtered. The filter cake was washed twice by tetrahydrofuran (50 g each); and after the filtrates were combined and distilled to recover tetrahydrofuran at a normal pressure, 100 g of water, 15 g of 30% hydrochloric acid, and 200 g of 1, 2-dichloroethane were added to the obtained solid. The mixture was then stirred to react at 20° C. to 25° C. for 2 hours. The solution was then separated, and the aqueous phase was extracted by 1, 2-dichloroethane (50 g each). The organic phases were combined. After the mixture was distilled to recover the solvent at a normal pressure, it was distilled at a reduced pressure to obtain 22.5 g of methyl N-benzylpiperidine-5-one-2S-carboxylate as colorless and transparent liquid in a GC purity of 99.8% and a yield of 91.1%.

Example 6: Preparation of Ethyl N-benzyl piperidine-5-one-2S-carboxylate ($V_2$)

To a 500 ml 4-neck flask equipped with a stirrer and a thermometer were charged 200 g of tetrahydrofuran, 7.5 g (0.11 mol) of sodium ethoxide, cooled to −5° C. to 0° C., and then added dropwise with 38.0 g (0.10 mol) of diethyl N-benzyl-N-ethoxycarbonylmethyl-L-glutamate (prepared in Example 2) at that temperature; after completion of the dropwise adding, the mixture was stirred to react at 20° C. to 25° C. for 4 hours, and then filtered. The filter cake was washed twice by tetrahydrofuran (50 g each); and then after the filtrates were combined and distilled to recover tetrahydrofuran at a normal pressure, 100 g of water, 15 g of 30% hydrochloric acid, and 200 g of 1, 2-dichloroethane were added to the obtained solid. The mixture was then stirred to react at 20° C. to 25° C. for 2 hours. The solution was then separated, and the aqueous phase was extracted by 1, 2-dichloroethane (50 g each). The organic phases were combined. After the mixture was distilled to recover the solvent at a normal pressure, it was distilled at a reduced pressure to obtain 24.4 g of ethyl N-benzylpiperidine-5-one-2S-carboxylate as colorless and transparent liquid in a GC purity of 99.7% and a yield of 93.5%.

Example 7: Preparation of Benzyl N-benzylpiperidine-5-one-2S-carboxylate ($V_3$)

To a 500 ml 4-neck flask equipped with a stirrer and a thermometer were charged 250 g of tetrahydrofuran, 4.1 g (0.1 mol) of 60% sodium hydride, cooled to −5° C. to 0° C., and then added dropwise with 56.5 g (0.10 mol) of dibenzyl N-benzyl-N-benzyloxycarbonylmethyl-L-glutamate (prepared according to the method in Example 3) at that temperature; after completion of the dropwise adding, the mixture was stirred to react at 20° C. to 25° C. for 5 hours, and filtered. The filter cake was washed twice by tetrahydrofuran (50 g each); and then after the filtrates were combined and distilled to recover tetrahydrofuran at a normal pressure, 100 g of water, 15 g of 30% hydrochloric acid, and 200 g of 1,2-dichloroethane were added to the obtained solid. The mixture was then stirred to react for 3 hours at a temperature ranging from 20° C. to 25° C. The solution was then separated, and the aqueous layer was extracted by 1, 2-dichloroethane (50 g each). The organic layers were combined. After the mixture was distilled to recover 1, 2-dichloroethane and benzyl alcohol at a normal pressure, it was distilled at a reduced pressure to obtain 30.6 g of benzyl N-benzylpiperidine-5-one-2S-carboxylate as yellowish and transparent liquid in a GC purity of 99.6% and a yield of 93.5%.

Example 8: Preparation of Methyl Piperidine-5-one-2S-carboxylate ($VI_1$)

To a 500 ml stainless steel pressure cauldron were charged 24.7 g (0.10 mol) of methyl N-benzylpiperidine-5-one-2S-carboxylate (prepared by Example 5), 200 g of methanol, 0.3 g of 5% palladium-on-carbon catalyst; after nitrogen replacement for three times, hydrogen was introduced; the hydrogen pressure was maintained at 0.2~0.3 MPa, and the reaction was carried out at 40° C. to 45° C. for 5 hours. The mixture was cooled to 20° C. to 25° C. After nitrogen replacement for three times, filtration was carried out to remove the palladium-on-carbon; the filtrate was then concentrated to recover methanol and toluene, and then distilled at a reduced pressure to obtain 15.1 g of methyl piperidine-5-one-2S-carboxylate as yellowish liquid in a GC purity of 99.8% and a yield of 96.2%.

Example 9: Preparation of Ethyl Piperidine-5-one-2S-carboxylate ($VI_2$)

To a 500 ml stainless steel pressure cauldron were charged 26.1 g (0.10 mol) of ethyl N-benzylpiperidine-5-one-2S-carboxylate (prepared in Example 6), 160 g of ethanol, 1.5 g of 50% Raney nickel catalyst; after nitrogen replacement for three times, hydrogen was introduced; the hydrogen pressure was maintained at 0.1~0.3 MPa, and the reaction was carried out at 50° C. to 55° C. for 5 hours. The mixture was cooled to 20° C. to 25° C. After nitrogen replacement for three times, filtration was carried out to remove the catalyst; the filtrate was then concentrated to recover ethanol and toluene, and distilled at a reduced pressure to obtain 16.5 g of ethyl piperidine-5-one-2S-carboxylate as yellowish liquid in a GC purity of 99.9% and a yield of 96.5%.

Example 10: Preparation of Piperidine-5-one-2S-carboxylic Acid (IX)

To a 500 ml stainless steel pressure cauldron were charged 32.3 g (0.10 mol) of benzyl N-benzylpiperidine-5-one-2S-carboxylate (prepared in Example 7), 200 g of methanol, and 0.4 g of 5% palladium-on-carbon catalyst; after nitrogen replacement for three times, hydrogen was introduced; the hydrogen pressure was maintained at 0.2~0.3 MPa, and the reaction was carried out at 40° C. to 45° C. for 6 hours. The mixture was cooled to 20° C. to 25° C. After nitrogen replacement for three times, filtration was carried out to remove the palladium-on-carbon; after the filtrate was concentrated to recover methanol and toluene, 14.0 g of piperidine-5-one-2S-carboxylic acid as yellowish liquid in a GC purity of 99.9% and a yield of 97.9% was obtained.

Example 11: Preparation of Methyl 5-benzyloxyiminopiperidine-2S-carboxylate ($VII_1$)

To a 500 ml 4-neck flask equipped with a stirrer, a thermometer, and a reflex condenser were charged 220 g of ethyl acetate, 25.0 g (0.16 mol) of methyl piperidine-5-one-2S-carboxylate (prepared according to the method in Example 8), 27.0 g (0.17 mol) of benzyloxyamine hydrochloride, and 18.2 g (0.18 mol) of triethylamine. The mixture was then stirred for reaction at 50° C. to 55° C. for 4 hours, and then cooled and added with 100 g of water; the solution was separated, and the organic phase was washed twice by saturated saline (25 g each). After the organic phase was distilled to recover the solvent, it was distilled at a reduced pressure to obtain 41.3 g of methyl 5-benzyloxy-iminopiperidine-2S-carboxylate as yellowish transparent liquid in a GC purity of 98.9% and a yield of 98.5%.

Example 12: Preparation of Ethyl 5-benzyloxyiminopiperidine-2S-carboxylate ($VII_2$)

To a 500 ml 4-neck flask equipped with a stirrer, a thermometer, and a reflex condenser were charged 250 g of 1,2-dichloroethane, 26.0 g (0.15 mol) of ethyl piperidine-5-one-2S-carboxylate (prepared according to Example 9), 26.0 g (0.16 mol) of benzyloxyamine hydrochloride, and 17.2 g (0.17 mol) of triethylamine. The mixture was then stirred for reaction at 50° C. to 55° C. for 4 hours, and then cooled and added with 100 g of water; the solution was separated, and the organic phase was washed twice by saturated saline (25 g each). After the organic phase was distilled to recover the solvent, it was distilled at a reduced pressure to obtain 40.8 g of methyl 5-benzyloxyiminopiperidine-2S-carboxylate as yellowish transparent liquid in a GC purity of 98.8% and a yield of 98.5%.

Example 13: Preparing of 5-benzyloxyiminopiperidine-2S-carboxylic Acid (X)

To a 500 ml 4-neck flask equipped with a stirrer, a thermometer, and a reflex condenser were charged 150 g of ethyl acetate, 14.3 g (0.10 mol) of piperidine-5-one-2S-carboxylic acid (prepared according to the method in Example 10), 19.0 g (0.12 mol) of benzyloxyamine hydrochloride, and 15.5 g (0.15 mol) of triethylamine. The mixture was then stirred for reaction at 60° C. to 65° C. for 4 hours, and then cooled and added with 100 g of water; the solution was separated, and the organic layer was washed twice by saturated salt water (25 g each). After the organic phase was distilled to recover the solvent, it was distilled to obtain 24.7 g of 5-benzyloxyiminopiperidine-2S-carboxylic acid as yellowish solid powder in an HPLC purity of 99.6% and a yield of 99.5%.

Example 14: Preparation of Methyl 5R-[(benzyloxy) amino] piperidine-2S-carboxylate ($II_{a1}$)

To a 500 ml 4-neck flask equipped with a stirrer and a thermometer were charged 200 g of ethyl acetate and 21.0 g (0.08 mol) of methyl 5-benzyloxyiminopiperidine-2S-carboxylate ($VII_1$, prepared according to the method in Example 11), and added 40.3 g (0.40 mol) of concentrated sulfuric acid dropwise at −20° C., and then stirred for 1 hour. 38.0 g (0.18 mol) of sodium triacetoxy borohydride was charged at −20° C., and then stirred to react at −20° C. to −15° C. for 5 hours. The mixture was kept at a temperature below 10° C., and then added with 100 g of water to quench the reaction, and neutralized by ammonium hydroxide. The solution was then separated, and the organic phase was washed twice by saturated saline (25 g each). After the organic phase was distilled to recover the solvent, 80 g of ethyl acetate, 40 g of methanol, and 10.4 g (0.08 mol) of oxalic acid dihydrate were charged to the remnant, and then heated to 45° C., stirred for 1 hour, and then cooled and filtered. The filter cake was first washed by 60 g of ethyl acetate/methanol (2:1) mixed liquid and then washed by 50 g of ethyl acetate. By vacuum drying, 18.0 g of single-isomer methyl 5R-[(benzyloxy) amino] piperidine-2S-carboxylate was obtained, in a chiral HPLC purity of 99.5% and a yield of 63.5%; when calculated on the basis of L-glutamic acid, the total yield is 50.0%.

Example 15: Preparation of Ethyl 5R-[(benzyloxy) amino] piperidine-2S-carboxylate ($II_{a2}$)

To a 500 ml 4-neck flask equipped with a stirrer and a thermometer were charged 200 g of ethyl acetate and 22.0 g (0.08 mol) of ethyl 5-benzyloxyiminopiperidine-2S-carboxylate ($VII_2$, prepared according to the method in Example 12), and added 40.3 g (0.40 mol) of concentrated sulfuric acid dropwise at −20° C., and then stirred for 1 hour. 38.0 g (0.18 mol) of sodium triacetoxyborohydride was charged at −20° C., and then stirred to react at −20° C. to −15° C. for 5 hours. The mixture was kept at a temperature below 10° C., and then added with 100 g of water to quench the reaction, and then neutralized by ammonium hydroxide. The solution was then separated, and the organic phase was washed twice by saturated saline (25 g each). After the organic phase was distilled to recover the solvent, 80 g of ethyl acetate, 40 g of methanol, and 10.4 g (0.08 mol) of oxalic acid dihydrate were charged to the remnant, followed by heating to 45° C., and then stirred for 1 hour, and then cooled and filtered. The filter cake was first washed by 60 g of ethyl acetate/methanol (2:1) mixed liquid and then washed by 50 g of ethyl acetate. By vacuum drying, 19.3 g of single-isomer ethyl 5R-[(benzyloxy) amino] piperidine-2S-carboxylate was obtained, in a chiral HPLC purity of 99.6% and a yield of 65.4%; when counted on the basis of L-glutamic acid, the total yield is 54.7%.

Example 16: Preparation of Methyl 5R-[(benzyloxy)amino]piperidine-2S-carboxylate ($II_{a1}$)

To a 500 ml 4-neck flask equipped with a stirrer and a thermometer were charged 300 g of ethyl acetate, 42.5 g (0.12 mol) of methyl 5R-[(benzyloxy)amino]piperidine-2S-carboxylate (prepared according to the method in Example 14), and 100 g (0.24 mol) of 20% sodium hydrogen carbonate solution, and then stirred for reaction at a temperature ranging from 30° C. to 35° C. for 2 hours. The solution was separated, and the aqueous phase was extracted twice by ethyl acetate (60 g each). The organic phases were combined and washed twice by the saturated sodium chloride solution (50 g each). After the solvent was recovered from the obtained organic phase, distilling at a reduced pressure was carried out to obtain 30.8 g methyl 5R-[(benzyloxy) amino] piperidine-2S-carboxylate with a GC purity of 99.8% and a yield of 97.3% as yellowish adhesive grease.

Example 17: Preparation of Ethyl 5R-[(benzyloxy) amino] piperidine-2Scarboxylate ($IIa_2$)

To a 500 ml 4-neck flask equipped with a stirrer and a thermometer were charged 300 g of ethyl acetate, 44.0 g (0.12 mol) of ethyl 5R-[(benzyloxy) amino] piperidine-2S-carboxylate (prepared according to the method in example 15), and 100 g (0.24 mol) of 20% sodium hydrogen carbonate solution, followed by stirring for reaction at 20° C. to 25° C. for 2 hours. The solution was separated, and the aqueous phase was extracted twice by ethyl acetate (60 g each). The organic phases were combined and washed twice by the saturated sodium chloride solution (50 g each). After the solvent was recovered from the organic phase, distilling at a reduced pressure was carried out to obtain 32.3 g of ethyl 5R-[(benzyloxy)amino]piperidine-2S-carboxylate as yellowish adhesive grease in a GC purity of 99.5% and a yield of 96.8%.

Example 18: Preparation of 5R-[(benzyloxy) amino] piperidine-2S-carboxylic Acid ($II_b$)

To a 500 ml 4-neck flask equipped with a stirrer and a thermometer were charged 100 g of water, 100 g of methanol, 31.7 g (0.12 mol) of methyl 5R-[(benzyloxy)amino] piperidine-2S-carboxylate (prepared according to the method of Example 16), and 30 g (0.15 mol) of 20% sodium hydroxide aqueous solution, followed by stirring for reaction at 30° C. to 35° C. for 3 hours; after the hydrolysis reaction was completed, the solution was acidified by 30% hydrochloric acid to adjust the pH value to a range from 6.0 to 7.0, followed by filtering and drying, thereby obtaining 29.3 g of 5R-[(benzyloxy) amino] piperidine-2S-carboxylic acid as white powder solid in an HPLC purity of 99.8% and a yield of 97.5%.

The NMR data of the product are provided below:
$^1$HNMR (400 MHz, DMSO-d6) δ: 1.26 (m, 1H), 1.45 (q, 1H), 1.80 (m, 1H), 2.11 (m, 1H), 3.03 (m, 2H), 3.20 (d, 1H), 4.58 (s, 2H), 6.77 (d, 1H), 7.29-7.37 (m, 5H).
$^{13}$C-NMR (400 MHz, DMSO-d6) δ: 25.96, 26.94, 46.11, 54.40, 59.37, 76.36, 127.99, 128.54, 128.63, 138.54, 169.36.

Example 19: Preparation of 5R-[(benzyloxy) amino] piperidine-2S-carboxylic Acid ($II_b$)

To a 500 ml 4-neck flask equipped with a stirrer and a thermometer were charged 100 g of water, 50 g of ethanol, 27.8 g (0.10 mol) of ethyl 5R-[(benzyloxy) amino] piperidine-2S-carboxylate (prepared according to the method of Example 17), and 24 g (0.12 mol) of 20% sodium hydroxide aqueous solution, followed by stirring for reaction at 40° C. to 45° C. for 3 hours; after the hydrolysis reaction was completed, the solution was acidified by 30% hydrochloric acid to adjust the pH value to a range from 2.5 to 3.0, followed by filtering and drying, thereby obtaining 24.5 g of 5R-[(benzyloxy) amino] piperidine-2S-carboxylic acid as yellowish powder solid in an HPLC purity of 99.9% and a yield of 98.0%.

Example 20: Preparation of 5R-[(benzyloxy) amino] piperidine-2S-carboxylic Acid ($II_b$)

To a 500 ml 4-neck flask equipped with a stirrer and a thermometer were charged 100 g of water, 100 g of methanol, 35.5 g (0.10 mol) of methyl 5R-[(benzyloxy)amino] piperidine-2S-carboxylate (prepared according to the method of Example 14), and 80 g (0.40 mol) of 20% sodium hydroxide aqueous solution, followed by stirring for reaction at 30° C. to 35° C. for 4 hours; after the hydrolysis reaction was completed, the solution was acidified by 30% hydrochloric acid to adjust the pH value to a range from 2.5 to 3.0, followed by filtering and drying, thereby obtaining 24.3 g of 5R-[(benzyloxy)amino]piperidine-2S-carboxylic acid as yellowish powder solid in an HPLC purity of 99.8% and a yield of 97.2%.

Example 21: Preparation of N-benzylpiperidine-5-one-2S-carboxylic Acid ($VIII_1$)

To a 500 ml 4-neck flask equipped with a stirrer and a thermometer were charged 100 g of water, 100 g of methanol, 24.7 g (0.10 mol) of methyl N-benzylpiperidine-5-one-2S-carboxylate (prepared according to the method of Example 5), and 24 g (0.12 mol) of 20% sodium hydroxide aqueous solution, followed by stirring for reaction at 40° C. to 45° C. for 4 hours; after the hydrolysis reaction was completed, the solution was acidified by 30% hydrochloric acid to adjust the pH value to a range from 2.5 to 3.0, followed by filtering and drying, thereby obtaining 22.9 g of N-benzylpiperidine-5-one-2S-carboxylic acid as yellowish powder solid in an HPLC purity of 99.7% and a yield of 98.3%.

Example 22: Preparation of Piperidine-5-one-2S-carboxylic Acid (IX)

To a 500 ml stainless steel pressure cauldron were charged 23.3 g (0.10 mol) of N-benzylpiperidine-5-one-2S-carboxylic acid (prepared by the method of Example 21), 120 g of methanol, 0.3 g of 5% palladium-on-carbon catalyst; after nitrogen replacement for three times, hydrogen was introduced; the hydrogen pressure was maintained at 0.1~0.3 MPa, and the reaction was carried out at 40° C. to 45° C. for 5 hours. The mixture was cooled to 20° C. to 25° C. After nitrogen replacement for three times, filtration was carried out to remove the palladium-on-carbon; after the filtrate was concentrated to recover methanol and toluene, 14.1 g of piperidine-5-one-2S-carboxylic acid as yellowish liquid in a GC purity of 99.9% and a yield of 98.6% was obtained.

Example 23: Preparation of 5R-[(benzyloxy)amino] piperidine-2S-carboxylic Acid (II$_b$)

To a 500 ml 4-neck flask equipped with a stirrer and a thermometer were charged 150 g of ethyl acetate and 20.0 g (0.08 mol) of 5-benzyloxyiminopiperidine-2S-carboxylic acid (prepared according to the method in Example 13), and added dropwise 40.3 g (0.40 mol) of concentrated sulfuric acid at −20° C., followed by stirring for 1 hour.

38.0 g (0.18 mol) of sodium triacetoxyborohydride was charged at −20° C., followed by stirring to react at −20° C. to −15° C. for 5 hours. The mixture was kept at a temperature below 10° C., and then added with 100 g of water to quench the reaction, followed by neutralization by ammonium hydroxide. The solution was then separated, and the organic phase was washed twice by saturated salt water (25 g each). The organic phase was concentrated to recover the solvent, then 80 g of ethyl acetate, 40 g of methanol, and 10.4 g (0.08 mol) of oxalic acid dihydrate were charged to the remnant, followed by heating to 45° C., stirring for 1 hour, and then cooling and filtering. The obtained filter cake was first washed by 60 g of ethyl acetate/methanol (2:1) mixed liquid and then washed by 50 g of ethyl acetate. The obtained filter cake was charged to another 500 ml 4-neck flask, followed by adding 100 g of water, 100 g of methanol, 80 g (0.4 mol) of 20% sodium hydroxide aqueous solution, and then stirring for reaction at 30° C. to 35° C. for 4 hours; after the hydrolysis reaction was completed, the solution was acidified by 30% hydrochloric acid to adjust the pH value to a range from 2.5 to 3.0; after filtering and drying, 13.5 g of 5R-[(benzyloxy) amino] piperidine-2S-carboxylic acid as yellowish powder solid was obtained in an HPLC purity of 99.6% and a yield of 67.5%.

Example 24: Preparation of Methyl N-benzyl-5-benzyloxyiminopiperidine-2S-carboxylate (XI$_1$)

To a 500 ml 4-neck flask equipped with a stirrer, a thermometer, and a reflex condenser were charged 180 g of ethyl acetate, 24.7 g (0.10 mol) of methyl N-benzylpiperidine-5-one-2S-carboxylate (prepared by the method in Example 5), 19.0 g (0.12 mol) of benzyloxyamine hydrochloride, and 15.5 g (0.15 mol) of triethylamine. The mixture was then stirred for reaction at 60° C. to 65° C. for 4 hours, and then cooled and added with 100 g of water; the solution was separated, and the organic phase was washed twice by saturated salt water (25 g each). After the solvent was recovered from the organic phase, 35.0 g of methyl N-benzyl-5-benzyloxyiminopiperidine-2S-carboxylate as yellowish solid powder was obtained in an HPLC purity of 99.5% and a yield of 99.5%.

Example 25: Preparation of Methyl N-benzyl-5R-[(benzyloxy) amino] piperidine-2S-carboxylate (XII$_1$)

To a 500 ml 4-neck flask equipped with a stirrer and a thermometer were charged 220 g of ethyl acetate and 28.2 g (0.08 mol) of methyl N-benzyl-5-benzyloxyiminopiperidine-2S-carboxylate (prepared according to the method in Example 24), and added dropwise 40.3 g (0.4 mol) of concentrated sulfuric acid at −20° C., followed by stirring for 1 hour.

38.0 g (0.18 mol) of sodium triacetoxyborohydride was charged at −20° C., followed by stirring to react at −20° C. to −15° C. for 5 hours. The mixture was kept at a temperature below 10° C., and then added with 100 g of water to quench the reaction, followed by neutralization by ammonium hydroxide. The solution was then separated, and the organic phase was washed twice using saturated salt water (25 g each). The organic phase was concentrated to recover the solvent, then 80 g of ethyl acetate, 40 g of methanol, and 10.4 g (0.08 mol) of oxalic acid dihydrate were charged to the remnant, followed by heating to 45° C., stirring for 1 hour, and then cooling and filtering. The filter cake was first washed by 60 g of ethyl acetate/methanol (2:1) mixed liquid, and then washed by 50 g of ethyl acetate; after drying, 23.2 g of methyl N-benzyl-5R-[(benzyloxy) amino] piperidine-2S-carboxylate as yellowish powder solid was obtained in an HPLC purity of 99.7% and a yield of 65.3%.

Example 26: Preparation of Methyl 5R-[(benzyloxy)amino]piperidine-2S-carboxylate (IIa$_1$)

To a 500 ml stainless steel pressure cauldron were charged 50 g of methanol, 100 g of ethyl acetate, 22.2 g (0.05 mol) of methyl N-benzyl-5R-[(benzyloxy)amino]piperidine-2S-carboxylate (prepared in Example 25), and 0.3 g of 5% palladium-on-carbon catalyst; after nitrogen replacement for three times, hydrogen was introduced; the hydrogen pressure was maintained at 0.2~0.3 MPa, and the reaction was carried out at 40° C. to 45° C. for 5 hours. After cooling to 20° C.~25° C. and nitrogen replacement for three times, filtration was carried out to remove the palladium-on-carbon; the filtrate was migrated to another 4-neck flask, followed by charging 50 g (0.12 mol) of 20% sodium hydroxide aqueous solution and stirring at 30° C. to 35° C. for 3 hours. The solution was separated, and the aqueous phase was extracted thrice by ethyl acetate (60 g each). The organic phases were combined and washed twice by the saturated sodium chloride solution (50 g each). After the solvent was recovered from the organic phase, distilling at a reduced pressure was carried out to obtain 12.8 g of methyl 5R-[(benzyloxy) amino] piperidine-2S-carboxylate as yellowish adhesive grease in a GC purity of 99.8% and a yield of 97.0%.

What is claimed is:

1. A method of preparing N-protecting group piperidine-5-one-2S-carboxylate, comprising steps of:
   (1) reacting L-glutamic acid with alcohol via esterification reaction in the presence of an acidic reagent to prepare compound III, namely diester of L-glutamic acid hydrochloride;
   (2) upon completion of step (1), distilling the reaction system to recover excess acidic reagent and alcohol, then adding the same alcohol as in step (1) to the remnant, and then successively adding a base, 2-haloacetate, and N-protecting agent, or successively adding the base, N-protecting agent, and 2-haloacetate; after twice substitution reactions, obtaining compound IV;
   (3) subjecting compound IV to intramolecular condensation into a ring under the action of a solvent and a strong base, to obtain compound V, namely, N-protecting group piperidine-5-one-2S-carboxylate;

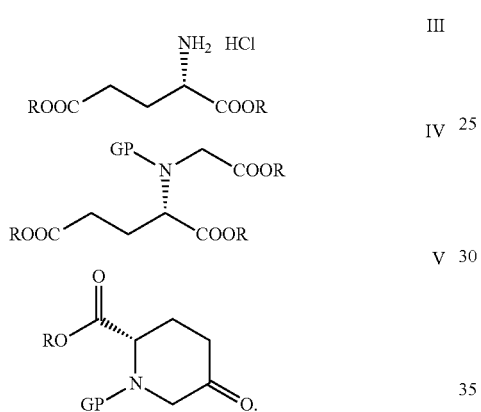

2. A method of preparing 5R-[(benzyloxy) amino] piperidine-2S-carboxylic acid or a derivative thereof, wherein 5R-[(benzyloxy) amino] piperidine-2S-carboxylic acid (II$_b$) or derivative thereof refers to 5R-[(benzyloxy) amino] piperidine-2S-carboxylate (II$_a$) or 5R-[(benzyloxy) amino] piperidine-2S-carboxylate oxalate (II$_c$), the method comprising steps of:
   (1) reacting L-glutamic acid with alcohol via esterification reaction in the presence of an acidic reagent to prepare compound III, namely diester of L-glutamic acid hydrochloride;
   (2) upon completion of the reaction of step (1), distilling the reaction system to recover excess acidic reagent and alcohol, then adding the same alcohol as in step (1) to the remnant, and then successively adding a base, 2-haloacetate, and N-protecting agent, or successively adding the base, N-protecting agent, and 2-haloacetate; after twice substitution reactions, obtaining compound IV;
   (3) subjecting compound IV to intramolecular condensation into a ring under the action of a solvent and a strong base, to obtain compound V, namely, N-protecting group piperidine-5-one-2S-carboxylate;
   the obtained compound V being used for preparing 5R-[(benzyloxy) amino] piperidine-2S-carboxylic acid (IIb) or its derivative, wherein a specific Route and corresponding steps are selected based on a target product: Route 1: compound V is subjected to removal of protecting group, condensation with benzyloxyamine hydrochloride, imine reduction-chiral resolution, neutralization, and hydrolysis; Route 2: compound V is subjected to hydrolysis, removal of protecting group, condensation with benzyloxyamine hydrochloride, imine reduction-chiral resolution, and neutralization; Route 3: compound V is subjected to condensation with benzyloxyamine hydrochloride, imine reduction-chiral resolution, removal of protecting group, neutralization, and hydrolysis.

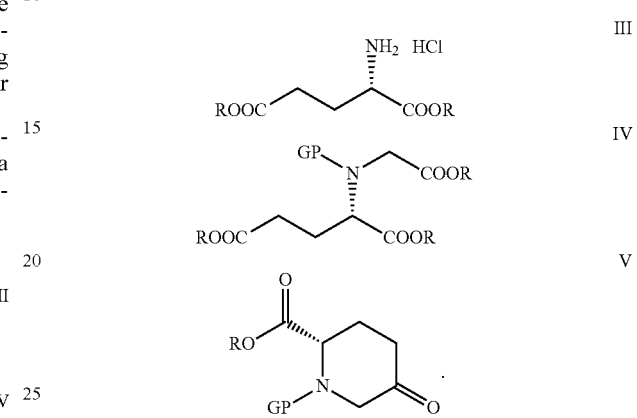

3. The method of preparing 5R-[(benzyloxy) amino] piperidine-2S-carboxylic acid or a derivative thereof according to claim 2, wherein Routes 1~3 comprise the following steps:
   Route 1:
   (1.1) subjecting the obtained compound V to removal of N-protecting group to obtain compound VI, namely piperidine-5-one-2S-carboxylate (VI);
   (1.2) condensing the obtained compound VI with benzyloxyamine hydrochloride in the presence of a solvent and a base to obtain compound VII;
   (1.3) subjecting the obtained compound VII to reduction with a reductant in ethyl acetate and in the presence of concentrated sulfuric acid, reacting the resultant product with added oxalate, and carrying out chiral resolution, to obtain 5R-[(benzyloxy) amino] piperidine-2S-carboxylate oxalate (II$_c$);
   (1.4) neutralizing the obtained 5R-[(benzyloxy) amino] piperidine-2S-carboxylate oxalate to obtain 5R-[(benzyloxy) amino] piperidine-2S-carboxylate (II$_a$);
   (1.5) subjecting the obtained 5R-[(benzyloxy) amino] piperidine-2S-carboxylate (II$_a$) to hydrolysis and acidification to obtain 5R-[(benzyloxy) amino] piperidine-2S-carboxylic acid (II$_b$);
   Route 2:
   (2.1) subjecting the obtained compound V to hydrolysis of ester group to obtain compound VIII, namely N-protecting group piperidine-5-one-2S-carboxylic acid (VIII);
   (2.2) subjecting compound VIII, namely, N-protecting group piperidine-5-one-2S-carboxylic acid, to removal of N-protecting group, to obtain piperidine-5-one-2S-carboxylic acid (IX);
   (2.3) condensing the obtained compound piperidine-5-one-2S-carboxylic acid (IX) with benzyloxyamine hydrochloride in the presence of a solvent and a base to obtain 5-benzyloxyiminopiperidine-2S-carboxylic acid (X);
   (2.4) subjecting the obtained compound X to reduction with a reductant in ethyl acetate and in the presence of concentrated sulfuric acid, reacting the resultant product with added oxalate, chiral resolution, and neutralization, to obtain 5R-[(benzyloxy) amino] piperidine-2S-carboxylic acid ($II_b$);

Route 3:

(3.1) condensing the obtained compound V with benzyloxyamine hydrochloride in the presence of a solvent and a base to obtain N-protecting group-5-benzyloxy-iminopiperidine-2S-carboxylate (XI);

(3.2) subjecting the obtained compound XI to reduction with a reductant in ethyl acetate and in the presence of concentrated sulfuric acid, reacting the resultant product with added oxalate, and carrying out chiral resolution, to obtain compound N-protecting group-5R-[(benzyloxy) amino] piperidine-2S-carboxylate (XII);

(3.3) subjecting the obtained compound XII to removal of N-protecting group and neutralization to obtain 5R-[(benzyloxy) amino] piperidine-2S-carboxylate ($II_a$);

(3.4) subjecting the obtained 5R-[(benzyloxy) amino] piperidine-2S-carboxylate ($II_a$) to hydrolysis and acidification to obtain 5R-[(benzyloxy) amino] piperidine-2S-carboxylic acid ($II_b$);

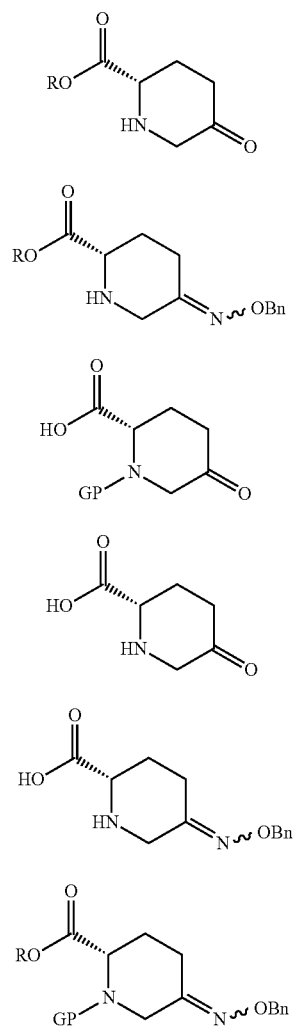

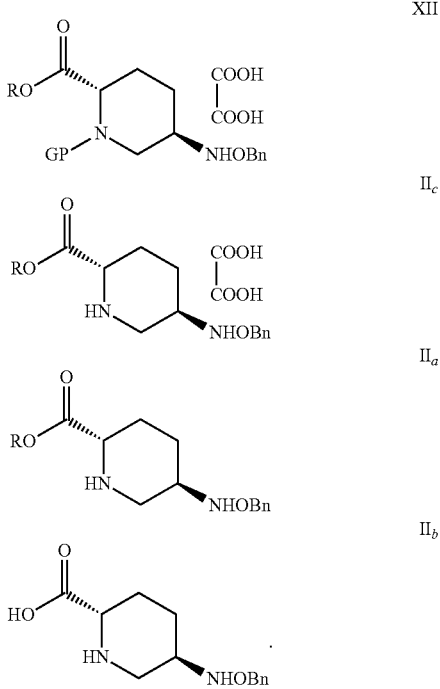

4. The method of preparing N-protecting group piperidine-5-one-2S-carboxylate according to claim 1, wherein in step (1), the acidic reagent in use is selected from the group consisting of thionyl chloride, phosgene, diphosgene, triphosgene, and oxalyl chloride, wherein when the acidic reagent is thionyl chloride or phosgene, a molar ratio of thionyl chloride or phosgene to L-glutamic acid is (2.1-4.5):1, wherein preferably a temperature for the esterification reaction ranges from 40° C. to 80° C., and a reaction duration ranges from 1 hour to 8 hours; when the acidic reagent is diphosgene or oxalyl chloride, a molar ratio of diphosgene or oxalyl chloride to L-glutamic acid is (1.1-2.5):1, wherein preferably the temperature for the esterification reaction ranges from 40° C. to 80° C., and the reaction duration ranges from 1 hour to 8 hours; when the acidic reagent is triphosgene, the molar ratio of triphosgene to L-glutamic acid is (0.7-1.5):1; wherein preferably the temperature for the esterification reaction ranges 60° C. to 80° C., and the reaction duration ranges from 1 hour to 8 hours; in step (1), a mass ratio of the alcohol to L-glutamic acid ranges from 8:1 to 30:1; the $C_{1-6}$ saturated fatty alcohol is selected from the group consisting of methanol, ethanol, n-propanol, isopropanol, n-butanol, isobutanol, tert-butanol, n-pentanol, isoamyl alcohol, tert-amyl alcohol, and hexyl alcohol; and the substituted $C_{6-9}$ aromatic alcohol or alkyl-substituted aromatic alcohol is selected from the group consisting of benzyl alcohol, o-methylbenzyl alcohol, and p-methylbenzyl alcohol.

5. The preparing method according to claim 1, wherein in step (2), the alcohol same as that added in step (1) refers to an alcohol of the same kind and quality; the base in step (2) refers to an inorganic base or an organic base, wherein the inorganic base is selected from the group consisting of potassium carbonate, sodium carbonate, calcium carbonate, potassium bicarbonate, sodium bicarbonate, calcium bicarbonate, potassium acetate, sodium acetate, and calcium acetate, or a combination thereof, and the organic base is selected from the group consisting of trimethylamine, triethylamine, and tri-n-butylamine, or a combination thereof; in step (2), the 2-haloacetate is selected from the group consisting of methyl 2-chloroacetate, methyl 2-bromoacetate, methyl 2-iodoacetate, methyl 2-iodoacetate, ethyl 2-chloroacetate, ethyl 2-bromoacetate, ethyl 2-iodoacetate, ethyl 2-iodoacetate, benzyl 2-chloroacetate, benzyl 2-bromoacetate, benzyl 2-iodoacetate, and benzyl 2-iodoacetate; in step (2), the N-protecting agent is selected from the group consisting of benzyl chloride, benzyl bromide, benzoyl chloride, methyl chloroformate, ethyl chloroformate, tert-butyl chloroformate, benzyl chloroformate, 9-fluorenylmethyl chloroformate, and di-tert-butyl dicarbonate; in step (2), the molar ratios of the 2-haloacetate, N-protecting agent, base and L-glutamic acid are (1.0-2.0):(1.0-2.0):(2.0-4.0): 1, respectively; preferably, the reaction temperature ranges from 40° C. to 70° C., and a duration of the two substitution reactions both ranges from 1 hour to 5 hours.

6. The preparing method according to claim 1, wherein in step (3), the strong base is selected from the group consisting of sodium hydride, sodium methoxide, sodium ethoxide, sodium tert-butoxide, potassium tert-butoxide or sodium benzylate; further preferably, a molar ratio of the strong base to compound IV is (1.0-2.0):1.

7. The preparing method according to claim 3, wherein in Route 1, the step (1.1) of subjecting the obtained compound V to removal of the N-protecting group to obtain compound VI is performed in the following manners based on different N-protecting groups: when the N-protecting group is benzyl, debenzylation is performed by catalytic hydrogenolysis; when the N-protecting group is benzoyl or alkoxycarbonyl, the corresponding N-protecting group is removed by hydrolysis under a basic condition; preferably, the catalyst used in the catalytic hydrogenolysis in step (1.1) is palladium on carbon or Raney nickel, and preferably, amount of the palladium on carbon catalyst is 0.5%~5% of the mass of compound V, and further preferably, the amount of the catalyst is 1%~3% by mass; preferably, amount of the Raney nickel is 1%~20% of the mass of compound V, and further preferably the amount of the catalyst is 5%~10% by mass; preferably, the solvent in step (1.1) is selected from the group consisting of methanol, ethanol, propanol, butanol, ethyl acetate, tetrahydrofuran, and acetonitrile, or a mixed solvent thereof, and further preferably, a mass ratio of the solvent to compound V ranges from 4:1 to 15:1; preferably, in step (1.1), a hydrogen pressure ranges from 0.1 Mpa to 1.0 MPa, a reaction temperature ranges from 20° C. to 85° C., and a reaction duration ranges from 3 hours to 10 hours; when the N-protecting group is benzoyl or alkoxycarbonyl, the corresponding N-protecting group is removed by hydrolysis under a basic condition; preferably, in step (1.1), the base is selected from the group consisting of potassium hydroxide, sodium hydroxide, and lithium hydroxide; a molar ratio of the base to compound V is (2.0-3.0):1; preferably, the solvent in step (1.1) is selected from the group consisting of water, methanol, ethanol, propanol, butanol, ethyl acetate, tetrahydrofuran, and acetonitrile, or a mixed solvent thereof, and further preferably, a mass ratio of the solvent to compound V ranges from 3:1 to 15:1; preferably, a temperature for the hydrolysis reaction in step (1.1) ranges from 10° C. to 100° C., and a reaction duration ranges from 2 hours to 10 hours; in step (1.2) of Route 1, the solvent is selected from the group consisting of methanol, ethanol, propanol, butanol, ethyl acetate, tetrahydrofuran, and acetonitrile, or a mixed solvent thereof, and further preferably, a mass ratio of the solvent to compound VI ranges from 3:1 to 15:1; in step (1.2), a molar ratio of benzyloxyamine hydrochloride to compound VI ranges from 0.9:1 to 1.5:1, wherein preferably the reaction temperature ranges from 10° C. to 80° C., the reaction duration ranges from 2 hours to 5 hours; in step (1.3), the concentrated sulfuric acid is a sulfuric acid with a mass fraction of 95%~98%, a molar ratio of the concentrated sulfuric acid to compound VII ranges from 3.0:1 to 6.0:1, and preferably, the concentrated sulfuric acid is a sulfuric acid with a mass fraction of 98%; in step (1.3), a mass ratio of ethyl acetate to compound VII is 5-20:1; further preferably, the mass ratio of ethyl acetate to compound VII ranges from 10-14:1; in step (1.3), the reductant is selected from the group consisting of sodium borohydride, sodium tricyanoborohydride, sodium triacetoxyborohydride, sodium tripropionyloxy borohydride, potassium borohydride, potassium tricyanoborohydride, potassium triacetoxyborohydride and potassium tripropionyloxy borohydride; a molar ratio of the reductant to compound VII is (2.0-4.0): 1; in step (1.4), the obtained 5R-[(benzyloxy) amino] piperidine-2S-carboxylate oxalate is neutralized with the base in the solvent to obtain 5R-[(benzyloxy) amino] piperidine-2S-carboxylate ($II_a$); in step (1.4), the solvent is selected from the group consisting of ethyl acetate, dichloromethane, chloroform, 1,2-dichloroethane, benzene, and methylbenzene, or a mixture thereof; preferably, a mass ratio of the solvent to compound $II_b$ ranges from 4:1 to 12:1; in step (1.4), the base is selected from the group consisting of potassium carbonate, sodium carbonate, calcium carbonate, potassium bicarbonate, sodium bicarbonate, calcium bicarbonate, and ammonium hydroxide or a combination thereof; preferably, the molar ratio of the base to 5R-[(benzyloxy) amino] piperidine-2S-carboxylate oxalate is (1.5-3.0):1; in step (1.4), a temperature for the neutralization reaction ranges from 10° C. to 40° C., and a reaction duration ranges from 2 hours to 5 hours; in step (1.5), the obtained 5R-[(benzyloxy) amino] piperidine-2S-carboxylate ($II_a$) is subjected to hydrolysis by the base in the solvent to obtain 5R-[(benzyloxy) amino] piperidine-2S-carboxylic acid ($II_b$); in step (1.5), the solvent is selected from the group consisting of water, ethyl acetate, dichloromethane, chloroform, 1,2-dichloroethane, benzene, and methylbenzene, or a mixture thereof; preferably, a mass ratio between the solvent and compound $II_a$ ranges from 4:1 to 12:1; preferably, in step (1.5), the base is selected from the group consisting of sodium hydroxide, potassium hydroxide, lithium hydroxide, potassium carbonate, sodium carbonate, calcium carbonate, potassium bicarbonate, and sodium bicarbonate, or a combination thereof; preferably, a molar ratio of the base to the 5R-[(benzyloxy) amino] piperidine-2S-carboxylate ($II_a$) is (1.5-3.0):1; in step (1.5), a temperature for the hydrolysis reaction ranges from 10° C. to 80° C., and a reaction duration ranges from 2 hours to 5 hours.

8. The preparing method according to claim 3, wherein in the step (2.1) of Route 2, compound V is hydrolyzed by a base in a solvent to obtain compound VIII, namely N-protecting group piperidine-5-one-2S-carboxylic acid (VIII); in step (2.1), the solvent is selected from the group consisting of water, ethyl acetate, dichloromethane, chloroform, 1,2-dichloroethane, benzene, and methylbenzene, or a mixture thereof; preferably, a mass ratio of the solvent to compound V ranges from 4:1 to 12:1; in step (2.1), the base is selected from the group consisting of sodium hydroxide, potassium hydroxide, lithium hydroxide, potassium carbonate, sodium carbonate, calcium carbonate, potassium bicarbonate, and sodium bicarbonate, or a combination thereof; preferably, a molar ratio of the base to compound V is (1.5-3.0):1; in step (2.1), a temperature for the hydrolysis reaction ranges from 10° C. to 80° C., and a reaction duration ranges from 2 hours to 5 hours; in step (2.2), the obtained compound VIII is subjected to removal of the N-protecting group to obtain compound IX, namely, piperidine-5-one-2S-carboxylic acid (IX); dependent on different N-protecting groups, one of the following manners is selected for removing the respective N-protecting group: when the N-protecting group is benzyl, debenzylation is performed by catalytic hydrogenolysis; when the N-protecting group is benzoyl or alkoxycarbonyl, the corresponding N-protecting group is removed by hydrolysis under a basic condition; preferably, the catalyst used in the catalytic hydrogenolysis in step (2.2) is palladium on carbon or Raney nickel, and preferably, amount of the palladium on carbon catalyst is 0.5%~5% of the mass of compound VIII, and further preferably, the amount of the catalyst is 1%~3% by mass; preferably, amount of the Raney nickel is 1%~20% of the mass of compound VIII, and further preferably the amount of the catalyst is 5%~10% by mass; preferably, the solvent in step (1.1) is selected from the group consisting of methanol, ethanol, propanol, butanol, ethyl acetate, tetrahydrofuran, and acetonitrile, or a mixed solvent thereof, and further preferably, a mass ratio of the solvent to compound VIII ranges from 4:1 to 15:1; preferably, in step (1.1), a hydrogen pressure ranges from 0.1 Mpa to 1.0 MPa, a reaction temperature ranges from 20° C. to 85° C., and a reaction duration ranges from 3 hours to 10 hours; when the N-protecting group is benzoyl or alkoxycarbonyl, the corresponding N-protecting group is removed by hydrolysis under a basic condition; preferably, in step (1.1), the base is selected from the group consisting of potassium hydroxide, sodium hydroxide, and lithium hydroxide; a molar ratio of the base to compound VIII is (2.0-3.0):1; preferably, the solvent in step (1.1) is selected from the group consisting of water, methanol, ethanol, propanol, butanol, ethyl acetate, tetrahydrofuran, and acetonitrile, or a mixed solvent thereof, and further preferably, a mass ratio of the solvent to compound VIII ranges from 3:1 to 15:1; preferably, a temperature for the hydrolysis reaction in step (1.1) ranges from 10° C. to 100° C., and a reaction duration ranges from 2 hours to 10 hours; in step (2.3), the solvent is selected from the group consisting of methanol, ethanol, propanol, butanol, ethyl acetate, tetrahydrofuran, and acetonitrile, or a mixed solvent thereof, and further preferably, a mass ratio of the solvent to compound IX ranges from 3:1 to 15:1; in step (2.3), a molar ratio of benzyloxyamine hydrochloride to compound IX ranges from 0.9:1 to 1.5:1, wherein preferably the reaction temperature ranges from 10° C. to 80° C., the reaction duration ranges from 2 hours to 5 hours; in step (2.4), the concentrated sulfuric acid is a sulfuric acid with a mass fraction of 95%~98%, a molar ratio of the concentrated sulfuric acid to compound X ranges from 3.0:1 to 6.0:1, and most preferably, the concentrated sulfuric acid is a sulfuric acid with a mass fraction of 98%; in step (2.4), a mass ratio of ethyl acetate to compound X is 5-20:1; further preferably, the mass ratio of ethyl acetate to compound X ranges from 10-14:1; in step (2.4), the reductant is selected from the group consisting of sodium borohydride, sodium tricyanoborohydride, sodium triacetoxyborohydride, sodium tripropionyloxy borohydride, potassium borohydride, potassium tricyanoborohydride, potassium triacetoxyborohydride and potassium tripropionyloxy borohydride; a molar ratio between the reductant and compound X is (2.0-4.0): 1.

9. The preparing method according to claim 1, wherein in step (3.1) of Route 3, the obtained compound V is condensed with benzyloxyamine hydrochloride in the presence of a solvent and a base to obtain compound XI, namely N-protecting group-5-benzyloxyiminopiperidine-2S-carboxylate (XI); in step (3.1), the solvent is selected from the group consisting of methanol, ethanol, propanol, butanol, ethyl acetate, tetrahydrofuran, acetonitrile, dichloromethane, chloroform, 1,2-dichloroethane, benzene, and methylbenzene, or a mixture thereof, and further preferably, a mass ratio of the solvent to compound V ranges from 3:1 to 15:1; in step (3.1), the base is selected from the group consisting of triethylamine, tri-n-butylamine, diisopropylethylamine, and piperidine, which are organic bases, and potassium carbonate, sodium carbonate, which are inorganic bases, or a mixture thereof, and a molar ratio of the base to compound V is (1.0-2.0):1; in step (3.1), a molar ratio of benzyloxyamine hydrochloride to compound V is 0.9-1.5:1; preferably, the reaction temperature ranges from 10° C. to 80° C., and the reaction duration ranges from 2 hours to 5 hours; in step (3.2), compound XI is subjected to reduction by a reductant in ethyl acetate and in the presence of concentrated sulfuric acid, reaction with added oxalate, and chiral resolution to obtain compound XII, namely, N-protecting group-5R-[(benzyloxy) amino] piperidine-2S-carboxylate (XII); in step (3.2), the concentrated sulfuric acid is a sulfuric acid with a mass fraction of 95%~98%, a molar ratio of the concentrated sulfuric acid to compound XI ranges from 3.0:1 to 6.0:1, and most preferably, the concentrated sulfuric acid is a sulfuric acid with a mass fraction of 98%; in step (3.2), a mass ratio of ethyl acetate to compound XI is 5-20:1; further preferably, the mass ratio of ethyl acetate to compound XI is 10-14:1; in step (3.2), the reductant is selected from the group consisting of sodium borohydride, sodium tricyanoborohydride, sodium triacetoxyborohydride, sodium tripropionyloxy borohydride, potassium borohydride, potassium tricyanoborohydride, potassium triacetoxyborohydride and potassium tripropionyloxy borohydride; the molar ratio of the reductant to compound XI is (2.0-4.0):1; in step (3.3), the obtained compound XII is subjected to removal of the N-protecting group and neutralization to obtain compound $II_a$, namely, 5R-[(benzyloxy) amino] piperidine-2S-carboxylate ($II_a$); dependent on different N-protecting groups, one of the following manners is selected to remove the respective N-protecting group: when the N-protecting group is benzyl, debenzylation is performed by catalytic hydrogenolysis; when the N-protecting group is benzoyl or alkoxycarbonyl, the corresponding N-protecting group is removed by hydrolysis under a basic condition; preferably, the catalyst used in the catalytic hydrogenolysis in step (3.3) is palladium on carbon or Raney nickel, and preferably, amount of the palladium on carbon catalyst is 0.5%~5% of the mass of compound XII and further preferably, the amount of the catalyst is 1%~3% by mass; preferably, amount of the Raney nickel catalyst is 1%~20% of the mass of compound XII, and further preferably the amount of the catalyst is 5%~10% by mass; preferably, the solvent in step (3.3) is selected from the group consisting of methanol, ethanol, propanol, butanol, ethyl acetate, tetrahydrofuran, and acetonitrile, or a mixed solvent thereof, and further preferably, a mass ratio of the solvent to compound XII ranges from 4:1 to 15:1; preferably, in step (3.3), a hydrogen pressure ranges from 0.1 Mpa to 1.0 MPa, a reaction temperature ranges from 20° C. to 85° C., and a total duration of deprotection and neutralization ranges from 3 hours to 10 hours; when the N-protecting group is benzoyl or alkoxycarbonyl, the corresponding N-protecting group is removed by hydrolysis under a basic condition; preferably, in step (3.3), the base is selected from the group consisting of potassium hydroxide, sodium hydroxide, and lithium hydroxide; a molar ratio of the base to compound XII is (2.0-3.0):1; preferably, the solvent in step (3.3) is selected from the group consisting of water, methanol, ethanol, propanol, butanol, ethyl acetate, tetrahydrofuran, and acetonitrile, or a mixed solvent thereof, and further preferably, a mass ratio of the solvent to compound XII ranges from 3:1 to 15:1; preferably, a temperature for the hydrolysis reaction in step (1.1) ranges from 10° C. to 100° C., and a reaction duration ranges from 2 hours to 10 hours; in step (3.4), the obtained 5R-[(benzyloxy) amino] piperidine-2S-carboxylate ($II_a$) is subjected to hydrolysis and acidification to obtain 5R-[(benzyloxy) amino] piperidine-2S-carboxylic acid ($II_b$); in step (3.4), the solvent is selected from the group consisting of water, ethyl acetate, dichloromethane, chloroform, 1,2-dichloroethane, benzene, and methylbenzene, or a mixture thereof; preferably, a mass ratio of the solvent to compound $II_a$ ranges from 4:1 to 12:1; in step (3.4), the base is selected from the group consisting of sodium hydroxide, potassium hydroxide, lithium hydroxide, potassium carbonate, sodium carbonate, calcium carbonate, potassium bicarbonate, and sodium bicarbonate, or a combination thereof; preferably, a molar ratio of the base to compound $II_a$ is (1.5-3.0):1; in step (3.4), a temperature for the hydrolysis reaction ranges from 10° C. to 80° C., and a reaction duration ranges from 2 hours to 5 hours.

10. The preparing method according to claim 2, wherein target product is prepared by selecting a corresponding route dependent on a specific target product and a specific protecting group; and avibactam and relebactam may be prepared from the obtained 5R-[(benzyloxy) amino] piperidine-2S-carboxylate ($II_a$), 5R-[(benzyloxy) amino] piperidine-2S-carboxylate oxalate ($II_c$), and 5R-[(benzyloxy) amino] piperidine-2S-carboxylic acid ($II_b$).

* * * * *